US008063089B2

(12) United States Patent
Mahadevan et al.

(10) Patent No.: US 8,063,089 B2
(45) Date of Patent: Nov. 22, 2011

(54) INHIBITORS OF NUCLEOPHOSMIN (NPM) AND METHODS FOR INDUCING APOPTOSIS

(75) Inventors: Daruka Mahadevan, Tucson, AZ (US); Wenqing Qi, Tucson, AZ (US); Bogdan Olenyuk, Tucson, AZ (US)

(73) Assignee: Arizona Board of Regents on Behalf of the University of Arizona, Phoenix, AZ (US)

( * ) Notice: Subject to any disclaimer, the term of this patent is extended or adjusted under 35 U.S.C. 154(b) by 287 days.

(21) Appl. No.: 12/039,551

(22) Filed: Feb. 28, 2008

(65) Prior Publication Data

US 2008/0221146 A1 Sep. 11, 2008

Related U.S. Application Data

(60) Provisional application No. 60/904,103, filed on Feb. 28, 2007.

(51) Int. Cl.
*A01N 43/52* (2006.01)
*A61K 31/415* (2006.01)
*C07D 235/00* (2006.01)

(52) U.S. Cl. .................................... 514/394; 548/304.4
(58) Field of Classification Search .................. 514/394; 548/304.4

See application file for complete search history.

(56) References Cited

U.S. PATENT DOCUMENTS

| | | | |
|---|---|---|---|
| 5,563,147 A | 10/1996 | Gilmore et al. | |
| 2002/0161022 A1 | 10/2002 | Reich et al. | |
| 2005/0009119 A1 | 1/2005 | Georges et al. | |
| 2007/0037841 A1 | 2/2007 | Nakatani et al. | |

FOREIGN PATENT DOCUMENTS

WO WO2007/056155 * 11/2005

OTHER PUBLICATIONS

Bleiberg, British Journal of Cancer, 1998, Cancer Research Campaign, vol. 77, Supplement 4, pp. 1-3.*
Williams et. al., Neoplasia, 1999, Stockton Press, vol. 1, No. 2, pp. 170-176.*
Romas, Current Medicinal Chemistry, 2006, Bentham Science Publ., vol. 13, pp. 1859-1876.*
Johnstone et. al., Cell, 2002, Cell Press, vol. 108, pp. 153-164.*
Miller et. al., Cancer and Metastasis Reviews, 2004, Kluwer Acad. Publ., vol. 23, pp. 119-135.*
Yang et. al., Polyhedron, 1995, Pergamon, vol. 14, No. 12, pp. 1565-1570.*
Wang, Hematology, 2003, American Society for Hematology, pp. 1-13.*
Wang et. al., European Journal of Nuclear Medicine, 1995, Springer-Verlag, vol. 22, No. 3, pp. 233-236.*
Takeharu Enomoto, et al., "Essential role of the B23/NPM Core Domain in Regulating ARF Binding and B23 Stability". Journal of Biological Chemistry, vol. 281, No. 27, Jul. 7, 2006, pp. 18463-18472.
Pui K, Chan, "Cross-linkage of Nucleophosmin in Tumor Cells by Nitrogen Mustard", Cancer Research, Jun. 15, 1989, pp. 3271-3275.
Haridasan V. M. Namboodiri et al., "The Structure and function of Xenopus No38-Core, a Histone Chaperone in the Nucleolus", Structure, vol. 12, Dec. 2004, pp. 2149-2160.
Chi Wai So. et al., "Dimerization: a versatile switch for oncogenesis", blood, vol. 104, No. 4, Aug. 15, 2004, pp. 919-922 and cover page.

* cited by examiner

*Primary Examiner* — Shengjun Wang
*Assistant Examiner* — Sarah Pihonak
(74) *Attorney, Agent, or Firm* — Oblon, Spivak, McClelland, Maier & Neustadt, L.L.P.

(57) ABSTRACT

Nucleophosmin inhibitors are disclosed which inhibit the multimerization of nucleophosmin and the biological activity of nucleophosmin, such as the ability of nucleophosmin to inhibit apoptosis and inhibit cellular differentiation. These small molecule inhibitors are useful for treating diseases and disorders, such as cancer associated with dysregulated nucleophosmin expression. Methods for identifying small molecule inhibitors of nucleophosmin involving multimerization sites for nucleophosmin are also disclosed. An exemplary small molecule inhibitor of nucleophosmin is NSC348884 which has the following chemical structure:

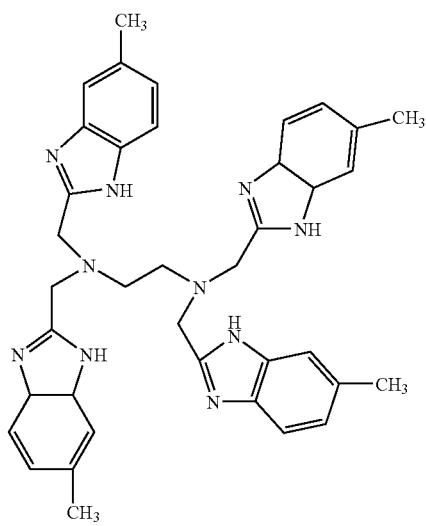

7 Claims, 20 Drawing Sheets
(9 of 20 Drawing Sheet(s) Filed in Color)

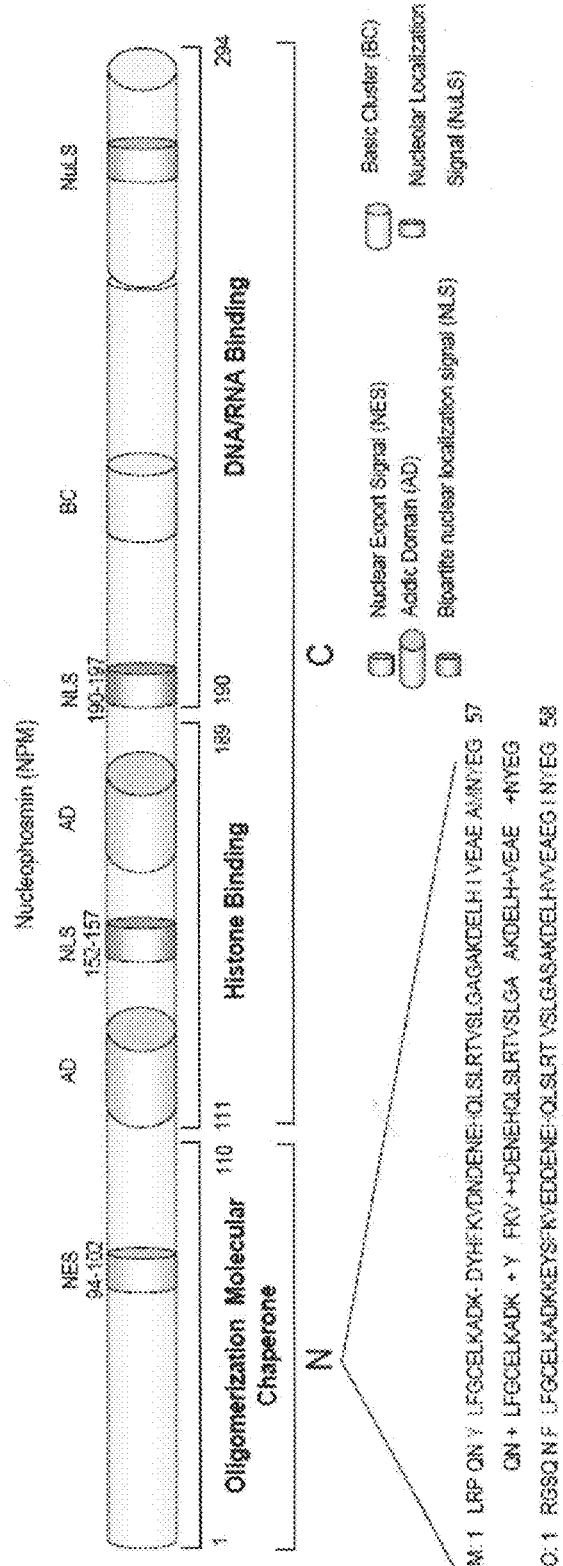

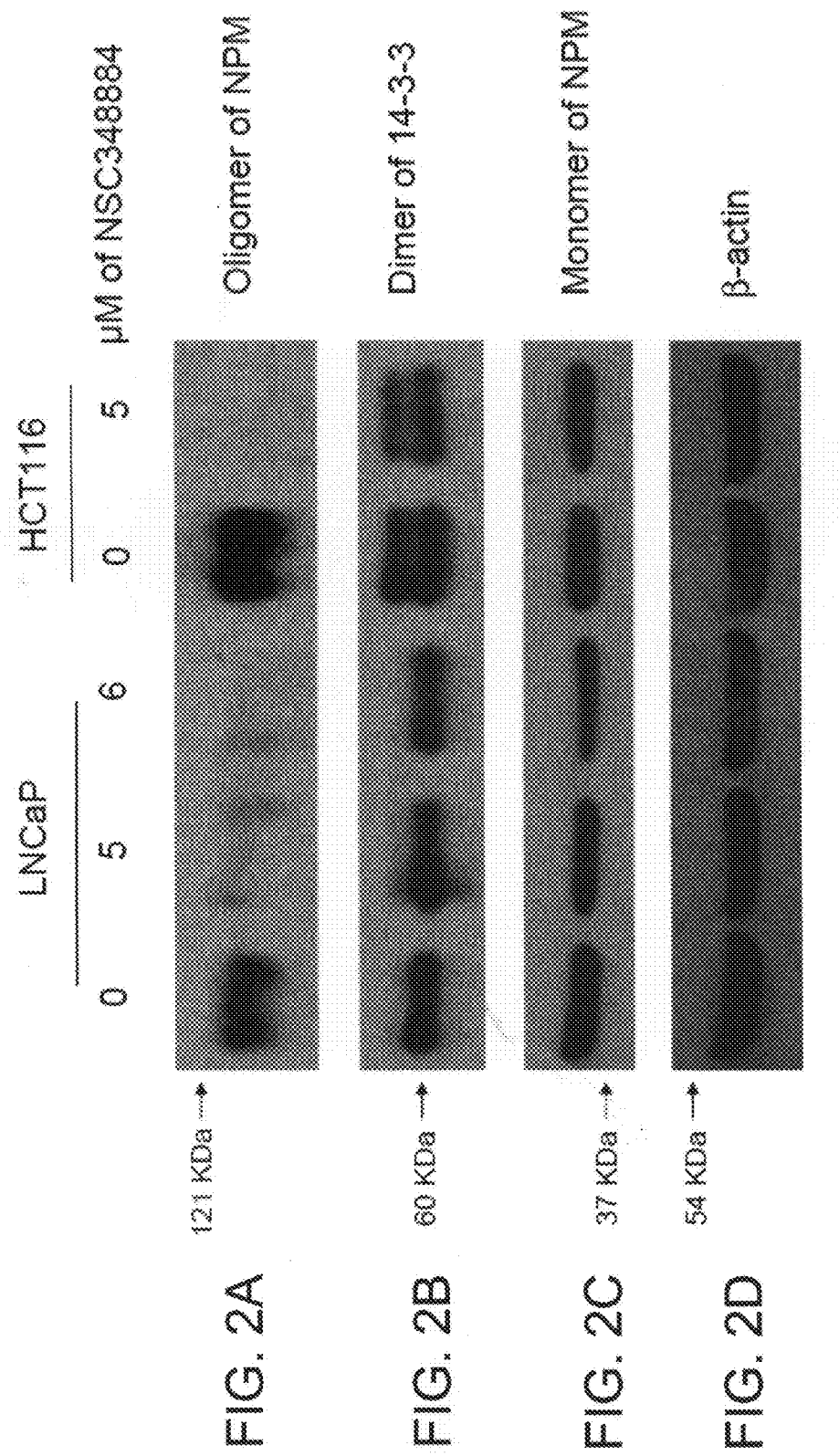

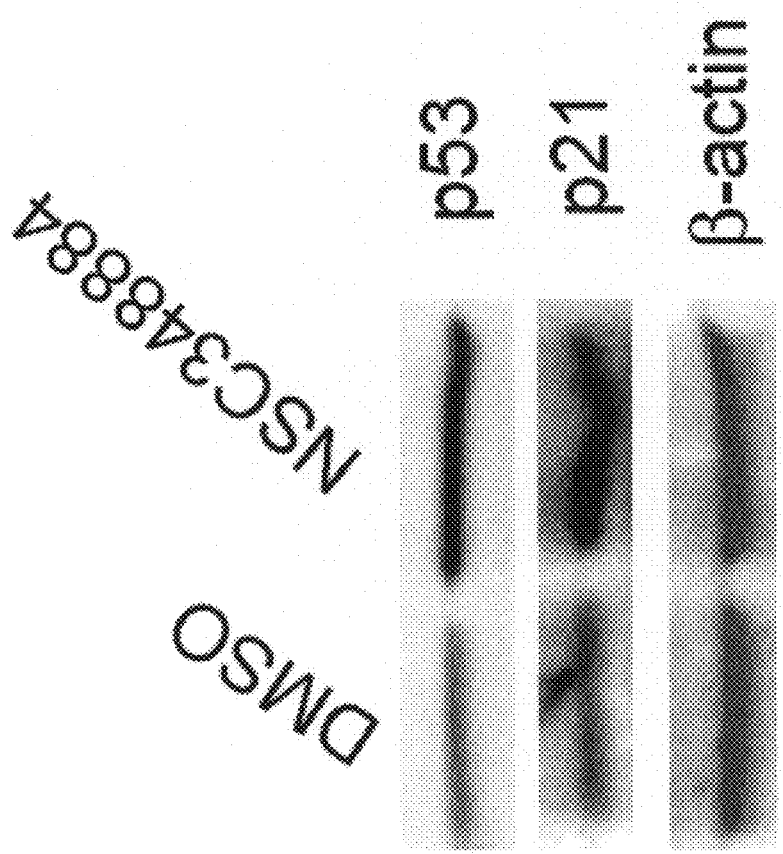

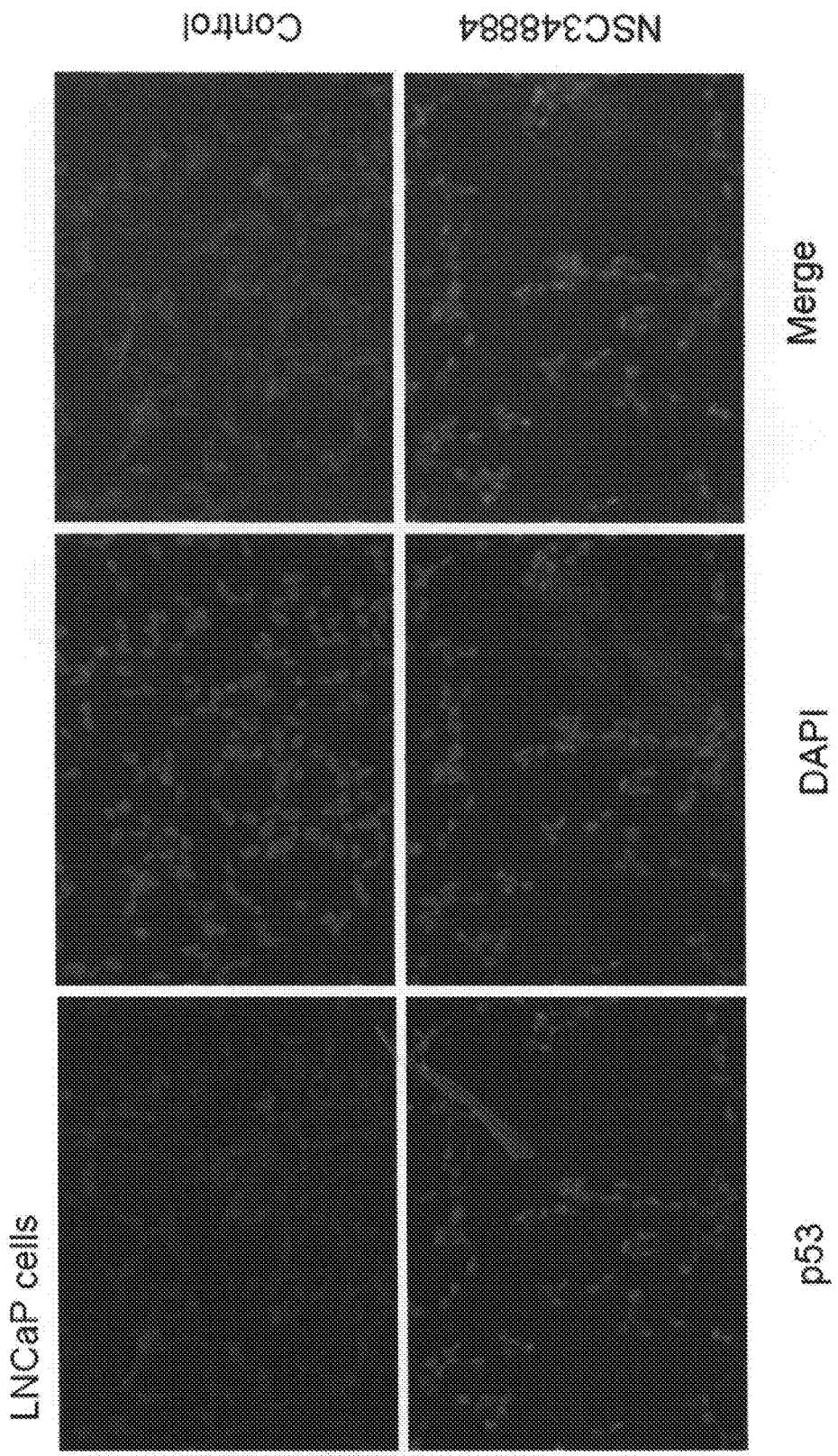

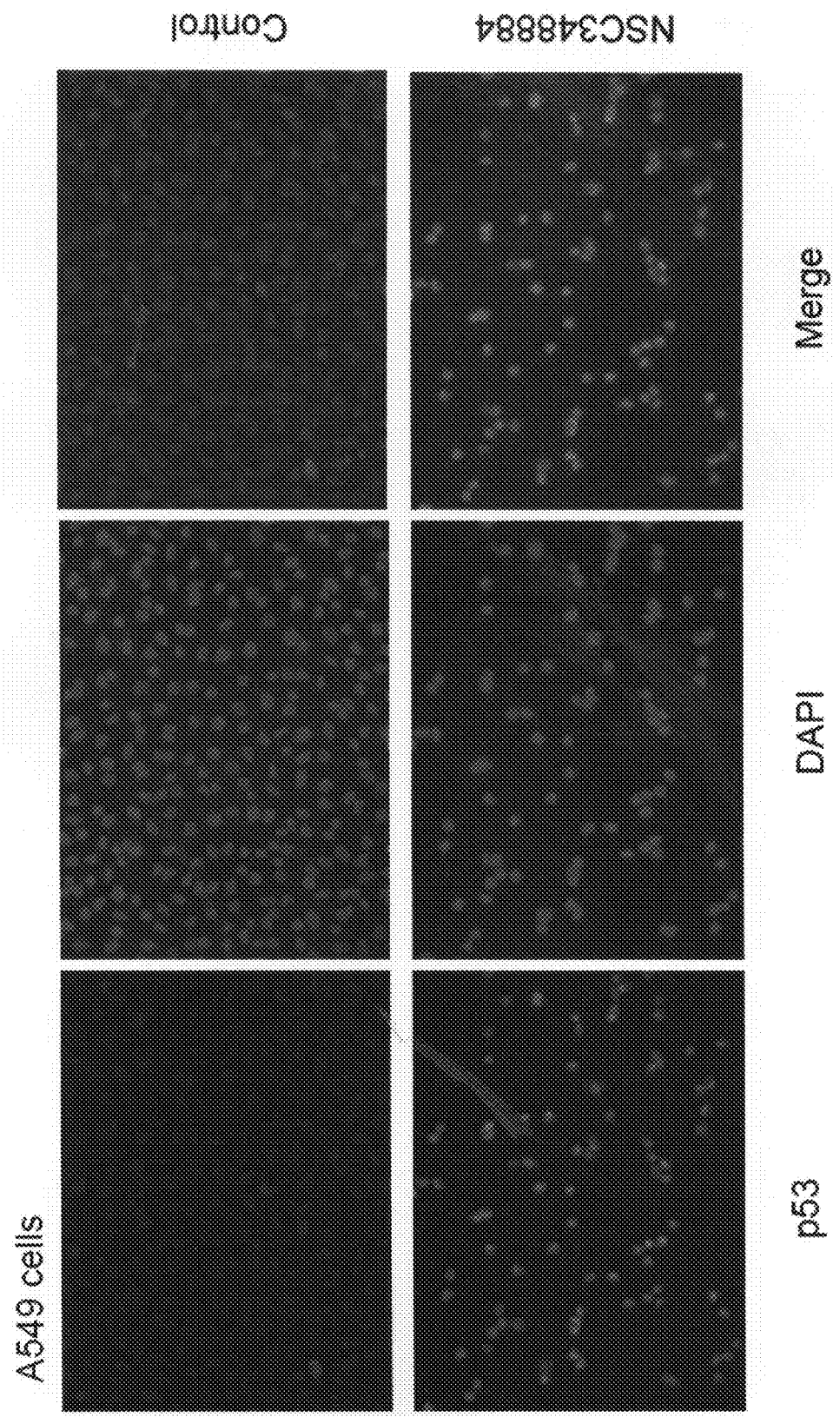

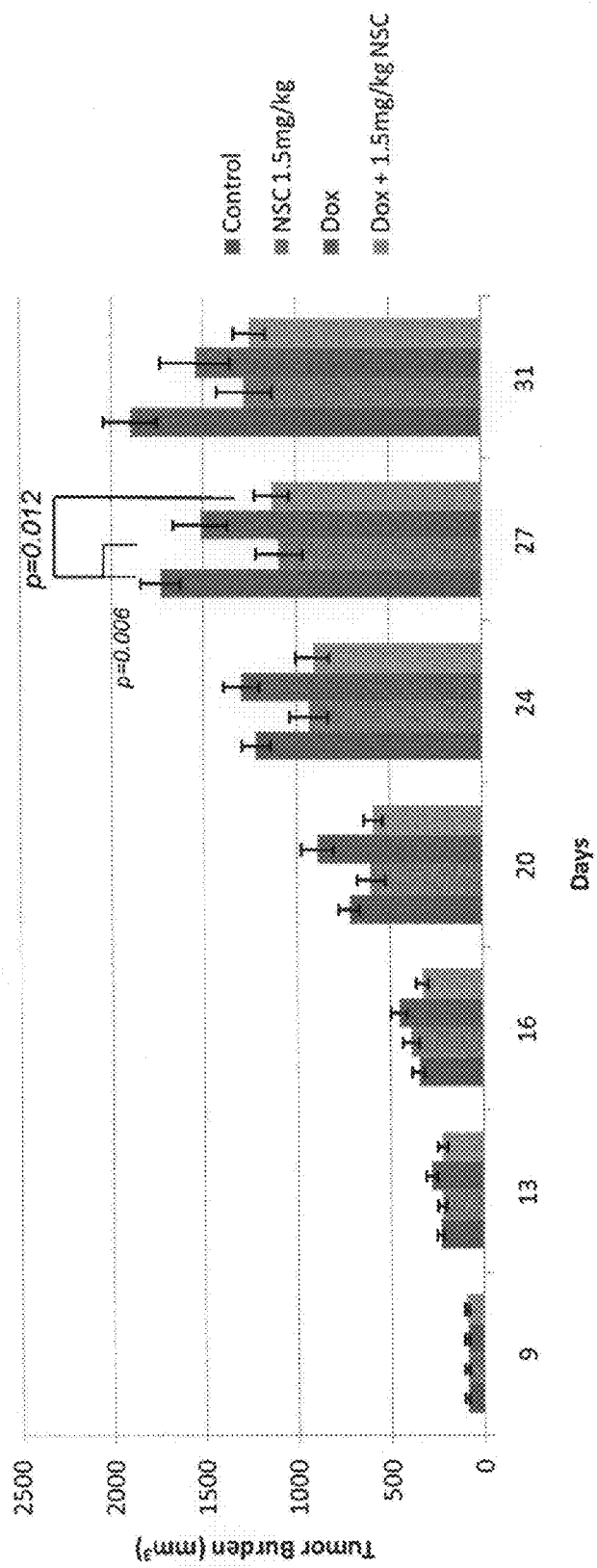

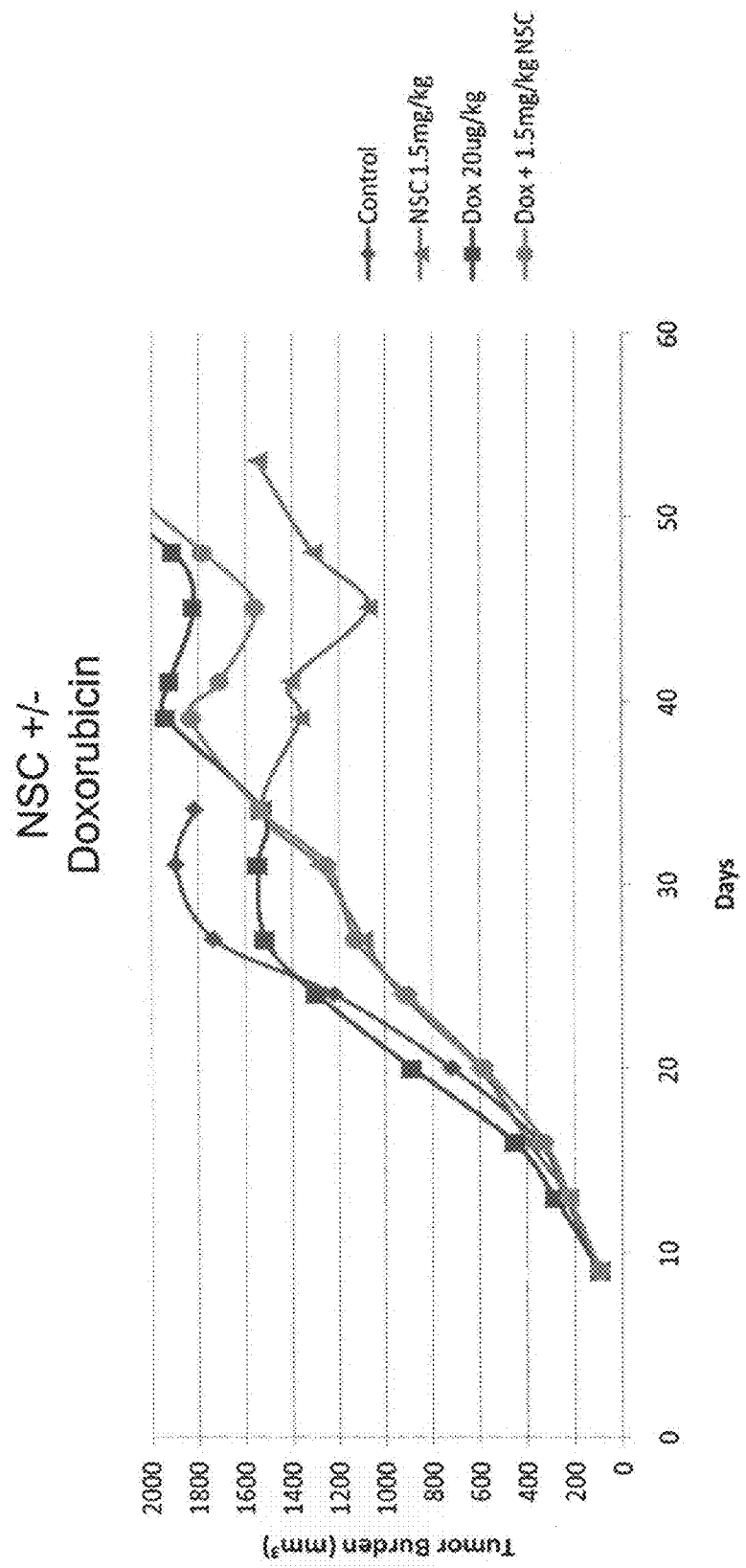

INHIBITORS OF NUCLEOPHOSMIN (NPM) AND METHODS FOR INDUCING APOPTOSIS

CROSS-REFERENCE TO RELATED APPLICATION

This application claims priority under 35 U.S.C. 119(e) to Provisional U.S. Application No. 60/904,103, filed Feb. 28, 2007, which is hereby incorporated by reference.

BACKGROUND OF THE INVENTION

1. Field of the Invention

The present invention relates to molecular inhibitors of Nucleophosmin (NPM) activity. NPM is a multifunctional nucleolar phosphoprotein that is dysregulated in human malignancies leading to anti-apoptosis and inhibition of differentiation. NPM inhibitors are useful for treating diseases or disorders associated with NPM-associated cellular dysregulation, such as cancer.

2. Description of the Related Art

Nucleophosmin (NPM), also known as B23, NO38, or numatrin (Lim and Wang, 2006), is a nucleolar phosphoprotein composed of an N-terminal globular domain (1-110 residues) and a C-terminal domain (111-294 residues) rich in acidic residues. NPM was initially identified as a critical player in ribosome biogenesis (Lim and Wang, 2006). Since then a number of cellular activities associated with NPM indicate that this protein has multiple functions, especially in cell proliferation, cytoplasmic/nuclear shuttle transportation, nucleic acid binding, ribonucleic cleavage, centrosome duplication and molecular chaperoning (Okuda, 2002; Okuwaki et al., 2001; Ye, 2005). NPM shuttles between the nucleolus and the cytoplasm, and it also translocates from the nucleolus to the nucleoplasm during the stationary phase of growth or during treatment with certain antitumor drugs (Chou and Yung, 1995; Yung et al., 1990).

Under native conditions, NPM exists as an oligomer (Herrera et al., 1996; Namboodiri et al., 2004). The structural features of NPM consist of an oligomerization domain, a metal-binding motif, a bipartitenuclear localization signal, phosphorylation sites and a nucleolar localization signal (Wang et al., 1993; Wang et al., 2005). Mounting evidence supports that NPM interacts with a variety of proteins including nucleolin (Li et al., 1996), cell cycle related protein p120 (Valdez et al., 1994), HIV-1 Rev protein (Fankhauser et al., 1991), HDM2 (Kurki et al., 2004), tumor suppressor ARF (Bertwistle et al., 2004; Itahana et al., 2003; Korgaonkar et al., 2005), p53 (Colombo et al., 2002; Li et al., 2004; Maiguel et al., 2004) and pRb (Takemura et al., 1999).

NPM has been found to be more abundant in tumor and growing cells than in normal resting cells (Chan et al., 1989; Feuerstein et al., 1988). In fact, NPM has been proposed as a tumor marker for prostate (Subong et al., 1999), colon (Nozawa et al., 1996), ovarian (Shields et al., 1997), gastric (Tanaka et al., 1992), and bladder (Yeh et al., 2006) cancers because NPM expression is markedly higher in these tumor cells than in the corresponding normal cells. Notably, overexpression of NPM in NIH3T3 cells results in malignant transformation (Kondo et al., 1997). NPM expression is down-regulated in cells undergoing differentiation or apoptosis (Patterson et al., 1995; van Belzen et al., 1995). However, overexpression of NPM leads to the inhibition of apoptotic cell death (Grisendi et al., 2006; Ye, 2005). In addition, NPM is frequently found in chromosomal translocations associated with hematological malignancies (Naoe et al., 2006).

The role of NPM as an oncogene is further enhanced as it binds several tumor suppressor genes, including pRb (Takemura et al., 1999), p14$_{ARF}$ (Brady et al., 2004; Gjerset, 2006; Lee et al., 2005; Zhang, 2004) and p53 (Colombo et al., 2002; Li et al., 2004; Maiguel et al., 2004). The p53/p14$_{ARF}$/Mdm2 (Hdm2) stress response pathway plays a central role in mediating cellular responses to oncogene activation, genome instability and therapy induced DNA damage. Recently, NPM emerged as a p14$_{ARF}$ binding protein and negative regulator of p53 by binding the same domains that mediate nucleolar localization and Hdm2 binding. This indicates that NPM may control p14$_{ARF}$ localization and compete with Hdm2 for ARF association. NPM knockdown markedly enhances ARF-Mdm2 association and diminishes ARF nucleolar localization. In addition, it has been shown that NPM directly interacts with p53 and down regulates its transcriptional activity (Maiguel et al., 2004). NPM binds to the p53 N-terminal end and prevents p53 phosphorylation at Ser15 in response to low doses of UV radiation. However, down regulation of NPM by small interfering RNA allowed p53 phosphorylation to occur. Similar results were observed in hematopoietic cells following ionizing irradiation treatments (Li et al., 2005) and in lymphoblasts exposed to hypoxia (Li et al., 2004). Together these data indicate that NPM is a natural repressor of p53 that may contribute to dampening p53 function during cellular growth or in the presence of DNA damage. Hence, NPM is an oncoprotein that if selectively targeted could be a potential therapy for cancer. An example of this concept is an NPM-binding peptide derived from the Rev protein which leads to cytotoxicity in Ras-transformed NIH-3T3 (Ras-3T3) cells, as well to inhibition of tumor growth in a nude mouse model (Chan et al., 2005).

Targeting protein-protein interaction sites as potential intervention points or 'hot spots' for the development of anti-cancer agents has made clear inroads and is now a reality (Arkin and Wells, 2004). This is due to the discovery of several specific small molecular agents targeting anti-apoptotic targets such as Bcl-2-Bax (Oltersdorf et al., 2005), MDM2-p53 (Vassilev et al., 2004) and XIAP-SMAC (Oost et al., 2004). Under native conditions, NPM exists as oligomers via its N-terminal molecular chaperone domain (Herrera et al., 1996; Hingorani et al., 2000; Namboodiri et al., 2004).

Over-expression of NPM prevents apoptosis induced by a variety of stimuli including hypoxia, radiation and retinoic acid (Grisendi et al., 2006; Ye, 2005). NPM is rapidly upregulated after UV irradiation resulting in resistance to UV-mediated apoptosis through enhanced DNA repair (Grisendi et al., 2006). As a nuclear PI(3,4,5)P$_3$ receptor, NPM inhibits DNA fragmentation activity of caspase-activated-DNase (CAD) and mediates an anti-apoptotic effect of nerve growth factor (NGF) (Ahn et al., 2005). In addition, NPM was found to target the interferon-inducible, double-stranded RNA-dependent protein kinase (PKR) and inhibit apoptosis (Grisendi et al., 2006). However, down regulation of NPM potentiates apoptotic cell death (Ye, 2005). A mouse NPM knockout experiment demonstrated that lack of NPM expression results in accumulation of DNA damage (Colombo et al., 2005).

Normally, the expression of cellular p53 protein is very low due to its relatively short half-life. Human MDM2 (HDM2) regulates p53 levels by binding to p53 and initiating proteasomal degradation (Oren, 1999). HDM2 also modulates several tumor suppressors, including p14$_{ARF}$. Recently, NPM emerged as a p4$_{ARF}$ binding protein and a negative regulator of p53 by binding to the same domains that mediate nucleolar localization and HDM2 binding. This indicates that NPM may control p14$_{ARF}$ localization and compete with HDM2 for p14$_{ARF}$ association. DNA damaging treatments disrupt the p14$_{ARF}$-NPM interaction and trigger a transient subnuclear redistribution of p14$_{ARF}$ to the nucleoplasm, where it interacts with HDM2 and prevents p53 degradation (Bertwistle et al., 2004; Gjerset, 2006; Korgaonkar et al., 2005; Lee et al., 2005). In addition, NPM has been shown to interact with the p53 N-terminal domain directly and inhibits p53 phosphorylation on Ser15 in response to low doses of UV radiation (Colombo et al., 2002; Maiguel et al., 2004). Collectively, the data indicate that NPM is a natural repressor of p53 that may contribute to dampening of p53 function during cellular growth or in the presence of low levels of DNA damage. In contrast, contradictory reports indicate that NPM stabilizes p53 by binding to HDM2 and protecting p53 from HDM2-mediated degradation (Kurki et al., 2004).

Administration of large molecule NPM inhibitors such as peptides or antibodies imposes many obstacles on treatment and makes it difficult to provide a convenient and economical pharmaceutical agent. There is a need to find simple, easily administered small molecules, such as those having molecular weights of less than 1,000 Daltons, that inhibit NPM functions associated with cellular dysregulation and malignancy. With these obstacles and goals in mind, the inventors sought out and identified particular classes of small molecules that inhibit NPM functions.

BRIEF DESCRIPTION OF THE INVENTION

The inventors have identified putative small molecule inhibitors of NPM multimerization, such as NSC348884, which targets NPM dimer formation. NSC348884 has efficient cytotoxicity on several different cancer cell lines by up-regulating p53 and p21 and inducing apoptosis. Nucleophosmin (NPM), a multifunctional nucleolar phosphoprotein is dysregulated in human malignancies leading to anti-apoptosis and inhibition of differentiation. NPM may be targeted by NSC348884 and other similar compounds to inhibit NPM functions involved in cancer. Such NPM inhibitors may be used alone or in combination with other types of cancer therapy, including chemotherapy.

Other aspects of the invention include pharmaceutical compositions containing the small molecule inhibitors of NPM functions, methods for treating diseases and disorders associated with these NPM functions by administering a small molecule inhibitor of NPM multimerization, as well as screening methods, including in silico pharmacophore-based, screening of small molecule libraries for molecules inhibiting NPM multimerization.

To identify small molecule inhibitors of the invention, the inventors studied the precise 3-dimensional structure of human NPM 1 based on the highly conserved structure of Xenopus NO38 and its requirement to form dimers and pentamers via its N terminal domain (residues 1-107). The inventors evaluated the precise 3-dimensional structure of NPM based on the highly conserved structure of Xenopus NO38 and its requirement to form dimers and pentamers via its N terminal domain (residues 1-107). It was found that small molecular inhibitors (SMI) could disrupt the formation of dimers and inhibit aberrant NPM function(s) in cancer cells. Molecular modeling, pharmacophore design, in silico screening and interactive docking identified NSC348884 as a putative NPM SMI that disrupts a defined hydrophobic pocket required for oligomerization. NSC348884 inhibited cell proliferation at an IC$_{50}$ of 1.7 to 4.0 µM in distinct cancer cell lines and disrupted NPM oligomer formation by native polyacrylamide gel electrophoresis assay. Treatment of several different cancer cell types with NSC348884 up-regulated p53 (increased Ser15 phosphorylation) and induced apoptosis in a dose-dependent manner that correlated with apoptotic markers: H2AX phosphorylation, PARP-cleavage and Annixin V labelling. Further, NSC348884 synergized doxorubicin cytotoxicity on cancer cell viability. The inventors have demonstrated that small molecule inhibitors of NPM oligomer formation, such as NSC34884 can up-regulate p21 and p53, induce apoptosis, and synergize with other types of cancer chemotherapy. Nucleophosmin (NPM) functions as an oncoprotein in certain cellular contexts and may be an important molecular target for cancer therapy. NSC348884 is the first putative SMI to target NPM discovered utilizing a structure-based design approach that disrupts dimer-oligomer formation. Similar to the inhibition of NPM by the Rev peptide and the down regulation of NPM by small interfering RNA, NSC348884, by binding and blocking the function(s) of NPM, induces apoptosis, up-regulates p53 and sensitizes cancer cells to doxorubicin treatment at sub-clinical doses. The inventors have found that a specific SMI that disrupts the formation of oligomers and inhibits NPM function(s) in cancer cells. In order to target human NPM with a SMI, the inventors evaluated the precise three-dimensional structure of NPM based on the highly conserved three dimensional structure of Xenopus NO38 and its requirement to form dimers and pentamers via its N-terminal domain (residues 1-110). Molecular modeling was utilized pharmacophore design, in silico screening of large databases and interactive docking to identify several putative NPM inhibitors that disrupt a defined hydrophobic pocket required for dimerization (FIG. 1). One of the compounds NSC348884 was selected and as predicted by modelling and interactive docking studies, disrupted NPM oligomer formation determined by native PAGE (FIG. 2). Therefore, a rapid, rational and reliable method that is recursive in the discovery of novel drugs for cancer therapy has been developed by the inventors. The data developed by the inventors shows that NPM suppresses p53 and blockage of NPM by NSC348884 enhances p53 activity (FIG. 5).

Using molecular modeling, pharmacophore design, in silico screening and interactive docking, the inventors have successfully identified a SMI of NPM (NSC348884). The effect of NSC348884 on growth inhibition is observed in many different cancer cell lines with distinct IC$_{50S}$ for cell viability based on the proliferative rate. Importantly, NSC348884 treatment sensitizes cells to doxorubicin and provides an excellent opportunity for combination therapies with lower doses of both drugs. Thus, targeting NPM by NSC348884 represents a potentially useful approach anticancer therapy.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIGS. 1A, 1B, 1C and 1D. Structure-based Drug Discovery of NPM Inhibitors. (FIG. 1A) Schematic of NPM and its functional domains: N-terminal residues (1-110) form the dimerization/oligomerization domain; residues 111-189 form the histone binding domain; residues 190-294 form the DNA/RNA binding domain. Within these domains reside functional motifs for nuclear export signaling, the acidic domain, bipartite nuclear localization signaling, the basic cluster, and nucleolar localization signaling. (FIG. 1B) Structure-based sequence alignment of human NPM with Xenopus NO38-core (pdb:1XE0) sequence predicts for a highly conserved N-terminal NPM domain. The residues in red (Y6, L7, F20, H29, M53, Y55, H104) are intimately involved in dimer formation and are essentially conserved except for residue F6 and 153 in Xenopus which are conservative changes (blue). (FIG. 1C) Homology model of human NPM N-terminal domain shows a highly conserved topology and interface predominantly of hydrophobic-aromatic interactions that promotes the formation of a dimmer and pentamer. NSC348884 a putative NPM inhibitor binds at the dimmer interface and interferes with dimerization. (FIG. 1D) Detailed interactions that NSC348884 makes with NPM are 2 hydrogen bonds with the backbone carbonyls of L7 and K21, an aromatic-aromatic interaction with Y6 and a potential hydrogen bond interaction with D25.

FIGS. 2A, 2B, 2C, 2D, and 2E. NSC348884 specifically disrupts NPM oligomer. (FIG. 2A) LNCaP and HCT116 cells were treated with NSC348884 at 0 (vehicle, DMSO), 5 and 6 µM for 24 hours and cell lysis was analyzed by native polyacrylamide gel electrophoresis. Immunoblotting was performed by utilizing the anti-NPM polyclonal antibody. (FIG. 2B) Using the same membrane of panel A to detect unrelated 14-3-3 proteins which exist as a dimer showed NSC348884 does not interfere with the 14-3-3 dimer formation. (FIG. 2C) The monomer level of NPM was determined by SDS-PAGE using the same samples as above. (FIG. 2D) β-actin was used as a loading control. (FIG. 2E) LNCaP cells were treated with vehicle or 5 µM of NSC348884 for 24 h. Oligomer and monomer of NPM were determined by native polyacrylamide gel electrophoresis.

(FIGS. 3A, 3B and 3C) MTT cell viability assays in triplicate were performed on the LNCaP prostate cell line and Granta (-4, -22 and -519) mantle cell lymphoma cell lines with varying concentrations of NSC348884 (0.01-60 µM for LNCaP and 0.5-2.8 µM for Granta cells) and Doxorubicin (0.0001-1 µM for Granta cells). NSC348884 was effective on LNCaP and Granta cells with an IC50 of ~4 µM and ~1.7 µM, respectively. The IC50 of doxorubicin on Granta cells was about 0.01-0.02 µM. (FIG. 3D) Synergistic effects of NSC348884 and Doxorubicin on Mantle Cell Lymphoma. NSC348884 at 1 µM or doxorubicin at 0.1 nM had no effect on cell viability but together was synergistic on all three Granta cell lines with near complete loss of viability, *p<0.003.

(FIG. 4A) LNCaP cells were treated with vehicle (DMSO), 1, 2, 3, 4 and 5 M of NSC348884 for 24 hours. Apoptosis was quantified by a fluorescent staining technique as described herein. The graph represents the mean percentage of apoptosis ±S.E. (n=3), *p<0.05. (FIG. 4B) Apoptosis was confirmed by immunoblotting to detect PARP cleavage and phosphorylation of H2AX in LNCaP after 2 h, 6 h and 24 h of NSC348884 treatment. (FIG. 4C and FIG. 4D). MCF7, PC-3, DU145 and Granta cells were treated with vehicle (DMSO) or 1 µM, 4 µM, and 5 µM of NSC348884 for 24 h. Cells were labeled by Annexin V and apoptosis was determined by flow cytometry analysis. X-axis: Annexin V-FITC, Y-axis: propidium iodide. The percentage of cells undergoing apoptosis is shown on right of each figure.

FIGS. 5A, 5B, 5C, and 5D. NSC348884 upregulates p53. (A) LNCaP cells were treated with NSC348884 at 0, 1, 2, 3, 4 and 5 µM for 2 h, 6 h and 24 h. Total p53 protein level and p53 phosphorylation on Ser 5 were evaluated by Western Blotting. Anti-β-actin was used as a loading control. (B) HCT116 cells were treated with vehicle or NSC348884 at 5 µM for 24 h. p53 and p21 protein levels were determined by Western Blotting. (C) LNCaP and A549 cells were treated with vehicle or 5 µM of NSC348884 for 6 h and fixed in cold methanol and acetone solution. Immunocytochemistry was performed shows red fluorescence representing p53 protein and nucleus was stained by DAPI to blue color (200×).

FIGS. 7A and 7B. Tumor burden in mice inoculated with HCT116 colon cancer cells and treated with NSC348884 (1.5 mg·kg) alone (▲), doxorubicin (20 mg/kg) alone (■), or doxorubicin+1.5 mg/kg NSC348884 (●) compared to control (◆).

DETAILED DESCRIPTION OF THE INVENTION

Figure 1C:
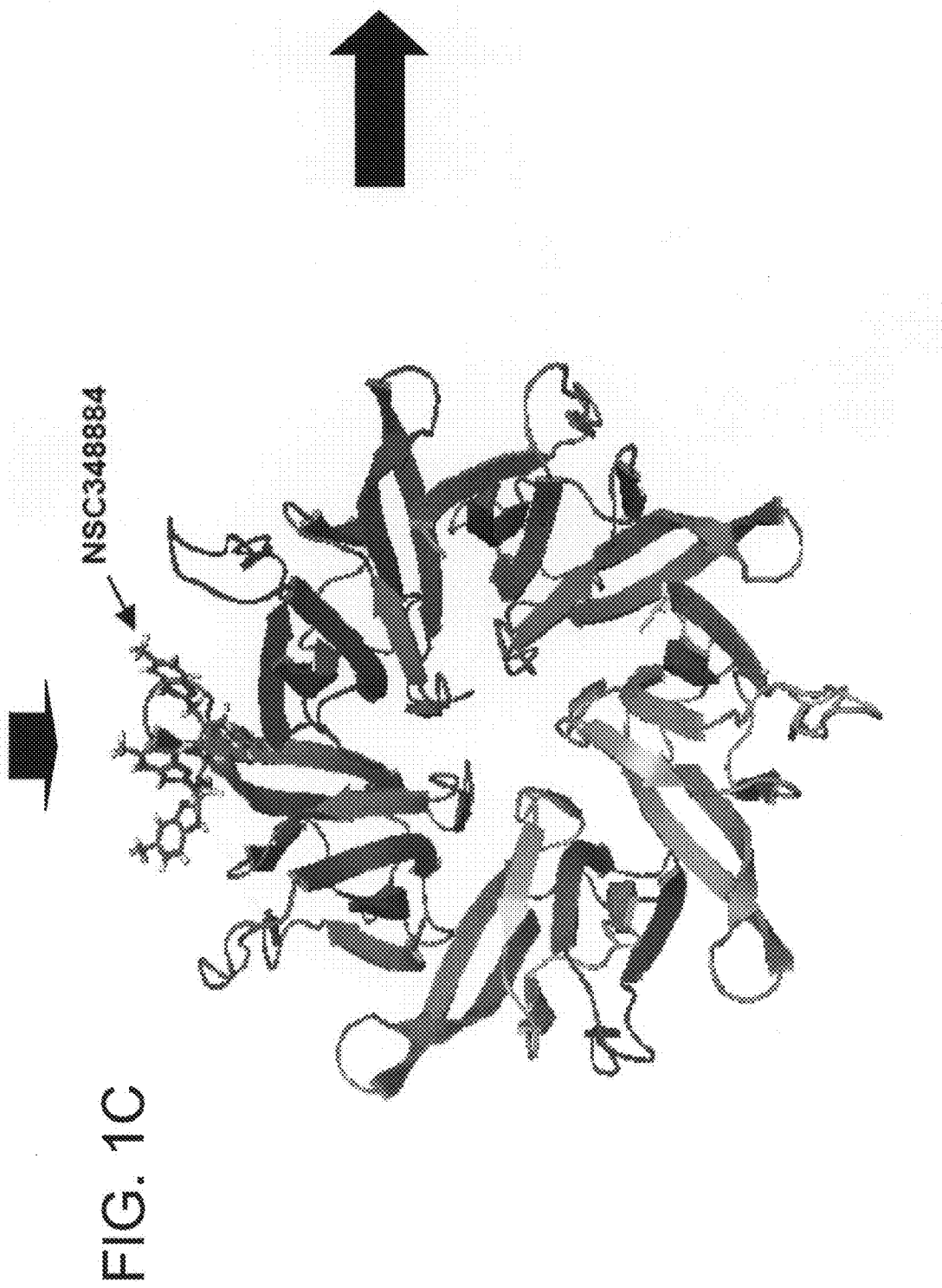

The small molecule inhibitors of nucleophosmin activity of the invention comprise at least two heterocyclic ring structures covalently-attached via a linker containing C, N and O atoms. Preferably, the at least two heterocyclic ring structures are linked via a backbone chain of 1-5, 1-10, or 1-15 atoms (or intermediary integer values). The term "backbone chain" refers the chain of atoms linking the heterocyclic rings together not taking into account side chains. The SMI compounds of the invention may conveniently contain the following central linker group:

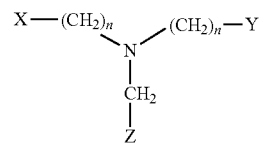

wherein at least two of X, Y and Z:

(i) participate in bonds to aromatic groups A, B and/or C which proceed through additional carbon, oxygen or nitrogen atoms, where any X, Y or Z not participating in a bond to a group A, B or C is substituted with hydrogen or lower aliphatic group, such as $C_1$-$C_6$ alkyl. For example, where Z is hydrogen the lower substituent above becomes methyl and X and Y are directly bonded or linked via intervening chemical groups to a Group (A), (B) and/or (C).

(ii) X and Y are bonds to aromatic groups (A), (B) and/or (C), where n is, independently, 1-15 (or any intermediate integer value within this range) and Z is hydrogen or lower aliphatic group, such as $C_1$-$C_6$ alkyl;

(iii) X and Y are bonds to an aromatic group (A), (B) and/or (C) where n=1-15 and Z is one or more alkylene groups —$(CH_2)_n$— where n is 0 to 6, which contain at least one nitrogen (N) or oxygen atom between the alkylene groups or between an alkylene group and (A), (B) and/or (C).

X, Y and Z are linked to groups (A), (B) and/or (C) via the $R_2$ bond of groups (A) and (B), or a bond at $R_4$ or $R_5$ on group (C).

Aromatic groups A, B and C are described below:
Group (A):

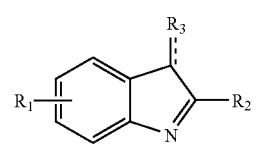

wherein

R$_1$ is one or more substituents selected from the group consisting of hydrogen, unsubstituted or substituted C$_1$-C$_6$ alkyl, C$_2$-C$_6$ alkenyl, C$_2$-C$_6$ alkynyl, C$_1$-C$_6$ alkoxy, aryl, and heteroaryl, which may be unsubstituted or substituted;

R$_2$ is a bond, and

R$_3$ is =O, =S, or hydroxyl.

A bond to hydrogen is implied at ring positions where no substitutent is indicated. Thus, when R3 is —OH, the other atom bonded to same ring carbon is hydrogen.

Group (B):

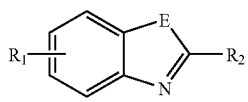

wherein

R$_1$ is one or more substituents selected from the group consisting of hydrogen, unsubstituted or substituted C$_1$-C$_6$ alkyl, C$_2$-C$_6$ alkenyl, C$_2$-C$_6$ alkynyl, C$_1$-C$_6$ alkoxy, aryl, and heteroaryl, which may be unsubstituted or substituted;

R$_2$ is a bond, and

E is a heteroatom selected from the group consisting of N, O and S.

Group (C):

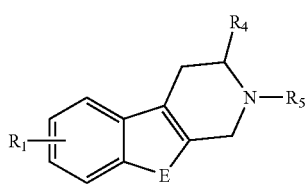

wherein

R$_1$ is one or more substituents selected from the group consisting of hydrogen, unsubstituted or substituted C$_1$-C$_6$ alkyl, C$_2$-C$_6$ alkenyl, C$_2$-C$_6$ alkynyl, C$_1$-C$_6$ alkoxy, aryl, and heteroaryl, which may be unsubstituted or substituted;

R$_4$ is a bond, or a moiety of formula (A) or (B),

R$_5$ is a bond, or unsubstituted or substituted C$_1$-C$_6$ alkyl, C$_2$-C$_6$ alkenyl, C$_2$-C$_6$ alkynyl, C$_1$-C$_6$ alkoxy, aryl, and heteroaryl, which may be unsubstituted or substituted; and E is a heteroatom selected from the group consisting of N, O and S.

A bond to hydrogen is implied at ring positions where no substitutent is indicated.

At least two and preferably at least three of Groups (A), (B) and/or (C) are linked together by a central linking group. The smi's of the invention may contain more than one group of type (A), (B) or (C) or different combinations of these groups. As described above, preferably the linking group will provide a spacer of 1-5, 1-10 or 1-15 contiguous "backbone" C, N and/or O atoms between substituents (A), (B) and/or (C). Generally, the backbone atoms are substituted with hydrogen or aliphatic substituents, such as methyl or ethyl. An example of a compound having the particular linking groups and Groups (A), (B) and (C) of the invention is NSC348884 which contains a dimethyl linker comprising >N—(CH$_2$)—(CH$_2$)—N< and 3 or 6 backbone atoms between the different groups (B):

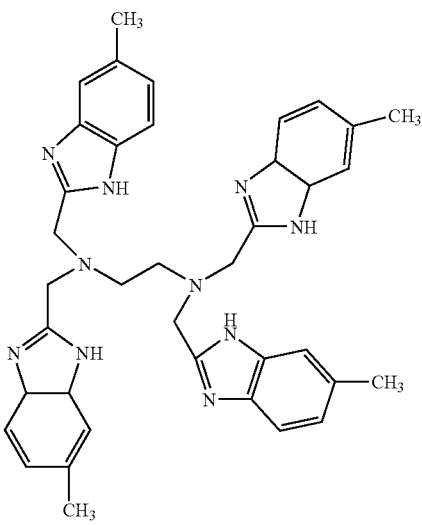

Other examples include analogs of NSC348884, such as those having 3, 4, 5 or 6 alkylene groups in between the two nitrogen atoms in the central linker, analogs containing 2, 3, 4, 5 or 6 alkylene groups between terminal Groups B and the nitrogen atoms in the central linker; analogs containing the heteroatoms O or S in the five membered rings of Groups B, and analogs having substituents other than methyl at position R$_1$ which are capable of hydrophobic interaction with amino acid residues in the multimerization site of NPM.

Still other examples are Compounds 2, 3 and 4 shown below:

Compound 2

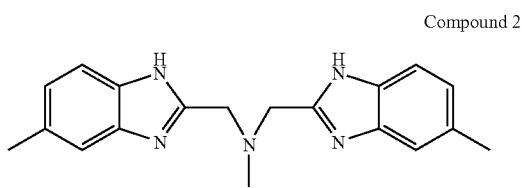

Chemical Formula: C$_{19}$H$_{21}$N$_5$
Molecular Weight: 319.40

N-methyl-1-(5-methyl-1H-benzo[d]imidazol-2-yl)-N-((5-methyl-1H-benzo[d]imidazol-2-yl)methyl)methanamine Compounds 3 and 4

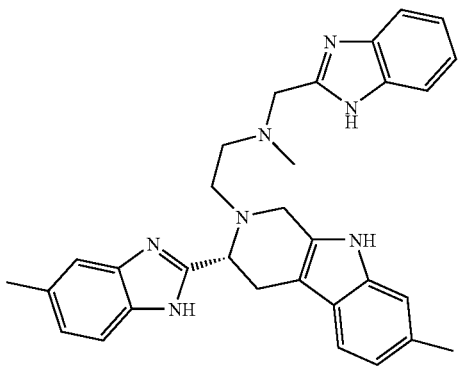

Compound 3
Chemical Formula: C$_{31}$H$_{33}$N$_7$
Molecular Weight: 503.64

(R)-N-((1H-benzo[d]imidazol-2-yl)methyl)-N-methyl-2-(7-methyl-3-(5-methyl-1H-benzo[d]imidazol-2-yl)-3,4-dihydro-1H-pyrido[3,4-b]indol-2(9H)-yl)ethanamine -continued

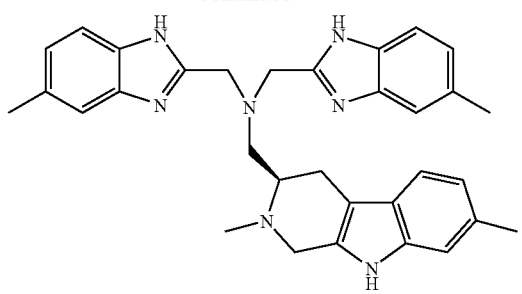

Compound 4

Chemical Formula: $C_{32}H_{35}N_7$
Molecular Weight: 517.67

1-(2,7-dimethyl-2,3,4,9-tetrahydro-1H-pyrido[3,4-b]indol-3-yl)-N,N-bis((5-methyl-1H-benzo[d]imidazol-2-yl)methyl)methanamine In addition the examples disclosed above, the small molecule inhibitors of NPM of the invention also include inhibitors such as Compounds 1, 5, 6 and 7 shown below where Group C is directly linked to at least one of Groups A, B or C:

Compounds 1 and 5

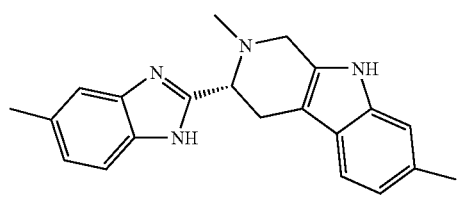

Chemical Formula: $C_{21}H_{22}N_4$
Molecular Weight: 330.43

(R)-2,7-dimethyl-3-(5-methyl-1H-benzo[d]imidazol-2-yl)-2,3,4,9-tetrahydro-1H-pyrido[3,4-b]indole

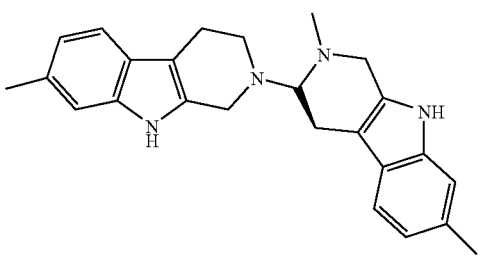

Chemical Formula: $C_{25}H_{28}N_4$
Molecular Weight: 384.52

(S)-2',7,7'-trimethyl-1,2',3,3',4,4',9,9'-octahydro-1'H-2,3'-bipyrido[3,4-b]indole Analogs of these compounds containing different hetero-groups in the five-membered ring structures, such as S and O, and substituents in place of the methyl group on the six-membered rings (such as those described above for $R_1$) that can interact with hydrophobic amino acids of the NPM multimerization site are contemplated.

Examples of analogs including oxygen as a heteroatom in one or both of the five-membered rings are shown below:

Compounds 6 and 7

Compound 6

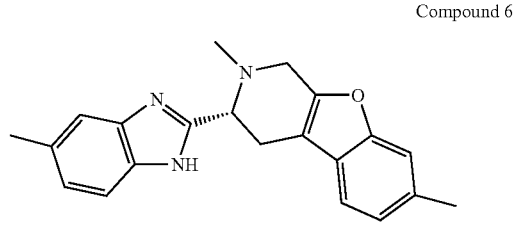

Chemical Formula: $C_{21}H_{21}N_3O$
Molecular Weight: 331.41

(R)-2,7-dimethyl-3-(5-methyl-1H-benzo[d]imidazol-2-yl)-1,2,3,4-tetrahydrobenzofuro[2,3-c]pyridine

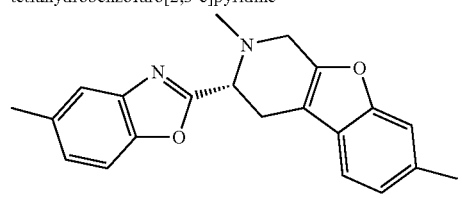

Chemical Formula: $C_{21}H_{20}N_2O_2$
Molecular Weight: 332.40

(R)-2,7-dimethyl-3-(5-methylbenzo[d]oxazol-2-yl)-1,2,3,4-tetrahydrobenzofuro[2,3-c]pyridine In addition to the linkers described above, analogs of the small molecular inhibitors of nucleophosmin multimerization may be produced using linkers comprising the following group to which at least two Groups A, B and/or C may be bound:

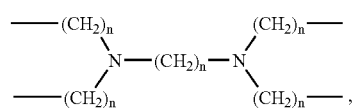

where n is, independently, 1, 2, 3, 4, 5 or 6. The terminal $(CH_2)_n$, groups may be present in a linear (e.g., —$CH_2$—$CH_2$—) configuration or may branch off of the adjacent nitrogen groups (as they do in NSC348884) providing two sites for attachment of Groups A, B and/or C. Examples of such a linker include:

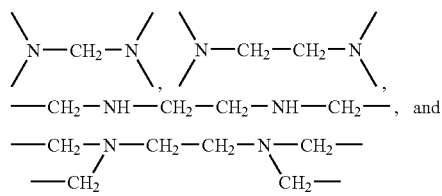

A linker may also comprise —$(CH_2)_n$—N—$(CH_2)_n$—N—$(CH_2)_n$—, where one or both of the nitrogen atoms (N) have been replaced by C. When replaced by C, the carbon will be substituted to valence with hydrogen and will be linked to one or more —$(CH_2)_n$— groups. In a branched configuration, the C will be linked to at least two —$(CH_2)_n$— groups. The terminal —(CH$_2$)$_n$— groups may be present in a linear (e.g., —CH$_2$—CH$_2$—) configuration or may branch off of the adjacent nitrogen groups (as they do in NSC348884) providing two sites for attachment of Groups A, B and/or C. Examples of such a linker include:

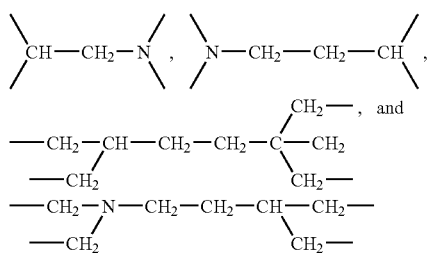

A linker can also encompass a structure as described above where 1 or both N's have been substituted with C further substituted with intervening oxygen atoms, such as —CH$_2$—CH$_2$—O—CH$_2$—CH$_2$— and a linear chain of repeated polyoxyethylene (—CH$_2$—CH$_2$—O—CH$_2$—CH$_2$—) chains. Examples include:

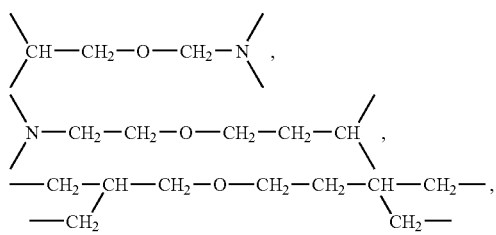

The small molecule inhibitors of the invention may incorporate the following structural modifications:

a. Replacing —N group of a dimethyl linker such as that in NSC348884, with —CH group as described above.

b. Replacing the —CH$_3$ groups in rings A, B and C with other aromatic, aliphatic groups or heterocycles arising from the aromatic ring structures of the compound.

c. Introduction of =O, =S or —OH or —SH groups emanating from the five membered ring structure in ring structures A, B and C.

d. Introduction of =O, =S or —OH or —SH groups emanating from the six-membered ring structure in ring structures A, B and C.

e. Replacing of one or several fused imidazole rings of the benzimidazoles in the core structure with oxazole or thiazole rings in ring structures A, B and C.

f. Replacing of one or several benzene rings of the benzimidazoles in the core structure with pyridine or pyrimidine rings in ring structures A, B and C.

g. Cyclization of one or several fragments of the core structure of the SMI to form substituted 1H-pyrido[3,4-b]indole or 1,3,4,9-tetrahydro-1H-pyrido[3,4-b]indole.

h. Cyclization of one or several fragments of the core structure of the SMI to form substituted 1H-1-pyrido[4,3-b]indole or 1,3,4,9-tetrahydro-1H-pyrido[4,3-b]indole.

i. Cyclization of one or several fragments of the core structure of the SMI to form substituted benzofuro[3,2-c]pyridine.

j. Cyclization of one or several fragments of the core structure of the SMI to form substituted 1,2,3,4-tetrahydrobenzofuro[3,2-c]pyridine.

k. Cyclization of one or several fragments of the core structure of the SMI to form substituted benzofuro[2,3-c]pyridine.

l. Cyclization of one or several fragments of the core structure of the SMI to form substituted 1,2,3,4-tetrahydrobenzofuro[2,3-c]pyridine.

m. Cyclization of one or several fragments of the core structure of the SMI to form substituted benzothiopheno[3,2-c]pyridine.

n. Cyclization of one or several fragments of the core structure of the SMI to form substituted 1,2,3,4-tetrahydrobenzothiopheno[3,2-c]pyridine.

o. Cyclization of one or several fragments of the core structure to form substituted benzothiopheno[2,3-c]pyridine.

p. Cyclization of one or several fragments of the core structure to form substituted 1,2,3,4-tetrahydrobenzothiopheno[2,3-c]pyridine.

The compounds of the invention may be further modified to improve their pharmacokinetics by methods known in the art. Such methods are also incorporated by reference to:

C. Hansch and A. Leo, *Exploring QSAR. Fundamentals and Applications in Chemistry and Biology*, American Chemical Society, Washington (1995).

C. Hansch and T. Fujita, Rho-sigma-pi analysis. A method for the correlation of biological activity and chemical structure, *J. Am. Chem. Soc.* 86 (1964), pp. 1616-1626.

D. A. Smith, H. Van de Waterbeemd and D. K. Walker, *Pharmacokinetics and Metabolism in Drug Design*, Wiley-VCH, New York (2001).

C. Hansch and W. J. Dunn III, Linear relationships between lipophilic character and biological activity of drugs, *J. Pharm. Sci.* 61 (1972), pp. 1-19.

D. E. Mager "Quantitative structure-pharmacokinetic/pharmacodynamic relationships." *Advanced Drug Delivery Reviews* 58 (2006), pp. 1326-1356.

W. J. Oreilly, "Pharmacokinetics and Clinical Chemistry—Review." *Pathology* 7 (1975), pp. 247-247.

A. M. Ruiz-Garcia, M. Bermejo, A. Moss, V. G. Casabo, "Pharmacokinetics in drug discovery." *Journal of Pharmaceutical Sciences* 97 (2008), pp. 654-690.

For example, the small molecule inhibitor NSC348884 can be modified by PEGylation or by glycosylation via an —OH group introduced onto the linker or one of Groups (B), see e.g., Veronese, et al., "PEGylation, successful approach to drug delivery." Drug Discovery Today 10(21): 1451-1458 (2005). As described by Veronese, et al. PEG-drug conjugates have several advantages: a prolonged residence in body, a decreased degradation by metabolic enzymes and a reduction or elimination of protein immunogenicity. The small molecule inhibitors of the invention may also be administered in the form of micelles, nanoparticles, or albumin particles, see e.g., Constantinides, et al., Adv. Drug. Deliv. Rev. 60(6): 757-67 (2008).

Pharmaceutical Compositions and Modes of Administration

The term "administer" includes any method of introducing the compositions of the present invention into a subject or exposing a subject to these compositions. This includes administration of prodrugs which convert into a compound of the invention when administered to a subject or which are otherwise treated to release an active form prior to administration. An example of a prodrug small molecule inhibitor would be one of the compounds of the invention which has been PEGylated or glycosylated. The term "pharmaceutically acceptable carrier" includes carriers and excipients such as solvents, dispersing agents, emulsions, lipid bilayers, liposomes, coatings, antibacterial or antifungal agents, isotonic agents, pH buffers, and absorption modulating agents, and other similar vehicles or carriers, compatible with a small molecule inhibitor of the invention and appropriate for pharmaceutical administration. Carriers, excipients and agents for administration of pharmaceutically active substances are well known in the art.

A pharmaceutical composition will generally formulated for compatibility with the intended route of administration (e.g., for oral, parenteral, oral, or topical administration). Other common routes of administration include intravenous (i.v.), intradermal, subcutaneous (s.c.), intracerebral, transmucosal, transdermal, by inhalation (e.g., intratracheal, intrapulmonary, or intrabroncial), intransal, oral, subuccal, transdermal, and rectal administration. A pharmaceutical composition when formulated for in vivo administration will generally include a sterile diluent, e.g., a liquid carrier such as water, normal saline, or other buffer compatible with an SMI of the invention. Buffers and isotonic agents may be present. pH may be adjusted using well known agents, such as HCl or NaOH. Antimicrobial agents may be added as well as antioxidants or other preservatives. Chelating agents, such as EDTA or EGTA, or dispersants or surfactants may be incorporated. The pharmaceutical composition may be prepared in unit dosages or in unit dose containers, such as vials, ampules, or syringes. Orally administered compositions can include a solid excipient or a liquid or gel excipient or carrier.

Methods of Using the Small Molecule Inhibitors of NPM Activity to Treat Cancer or Neoplasms The small molecule NPM inhibitors of the invention as described above may be used to prepare pharmaceutical compositions for administration to subjects having a disease or disorder mediated by or associated with an activity of NPM inhibited by the smi. The activity of NPM, even in a form expressed by a mutated or translocated NPM gene, may be regulated by the SMI of the invention when the NPM contains an intact oligomerization domain.

NPM is over-expressed in the cells of colon cancer, prostate cancer, ovarian cancer, breast cancer, gastro-esophageal cancer, pancreas cancer, bladder cancer, lung cancer, leukemia (acute and chronic), lymphoma, multiple myeloma, myelodysplastic syndrome, sarcoma, kidney cancer, carcinoma of unknown primary, and GBM. The NPM gene is translocated (and expresses a fusion protein comprising an NPM oliogmerization domain) in several diseases including leukemia, MDS, CML, and T-cell lymphoma. In addition, the NPM gene is mutated in certain malignant diseases, such as leukemia, but can express a mutated NPM protein containing an oligomerization domain. Since the SMI of the invention inhibit NPM activity by interfering with oligomerization of its domains, they are useful for inhibiting NPM activity in these types of malignant cells. Inhibition of NPM is also useful in the treatment of solid tumors. As shown in the example of in vivo treatment of malignant cells below, inhibition of NPM activity provides a significant survival advantage for treated animals.

The small molecule NPM activity inhibitors of the invention can be combined with chemotherapy (platins, etoposide, gemcitabine, taxols, anthracyclins, vincas, anti-metabolites, alkylating agents etc), targeted small molecule (erlotinib, sunitinib, imatinib, dasatinib, sorafenib, etc.) and monoclonal antibody therapy (rituximab, herceptin, cetuximab, bevacizumab) and anti-sense RNA therapy (Bcl-2, XIAP etc). Such combination therapy is exemplified below in Example 6, where the small molecule inhibitor NSC348884 is combined with other anticancer drugs.

Methods for Preparing the Small Molecule NPM Inhibitors of the Invention

The compounds of the invention may be produced by methods well known in the chemical arts. Exemplary methods are described below.

General Procedure for Preparation of NSC348884

N,N,N',N'-tetrakis[(5-methyl-2-benzimidazolyl)methyl]-1,2-ethanediamine (NSC348884) is known in the art. It is prepared by condensation of 4-methyl-1,2-phenylenediamine with ethylenedinitrilotetraacetic acid (EDTA) as outlined in the scheme below:

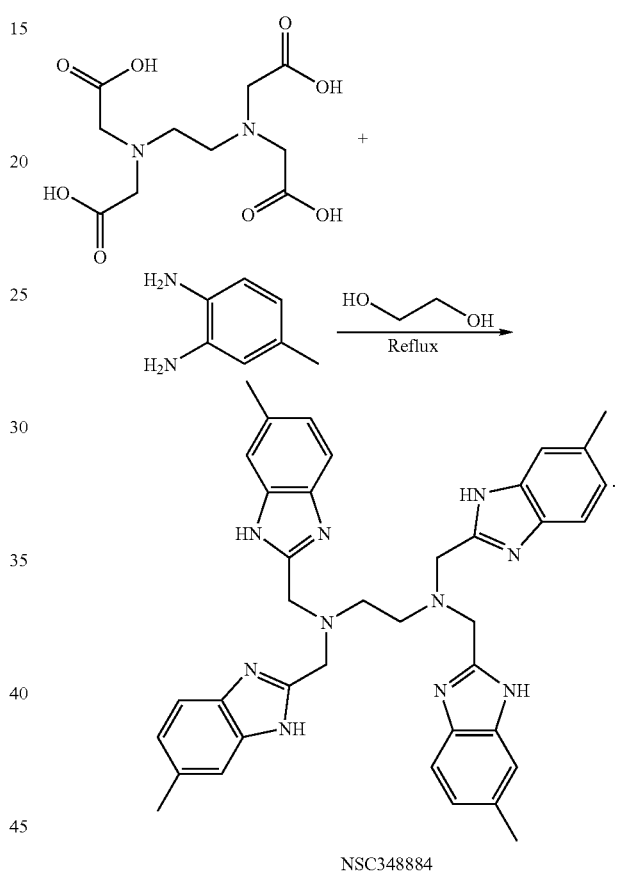

NSC348884

The condensation involves mixing of one equivalent of EDTA with four equivalents of 4-methyl 1,2-phenylenediamine in ethylene glycol. The mixture is then refluxed for 3 hours, then cooled. The crude product is crystallized when water was added to the cooled reaction mixture (it is important not to add water to hot ethylene glycol). The pure compound was obtained from the crude mixture by recrystallization from absolute ethanol. Methods for producing the compounds of the invention are also incorporated by reference to Hendriks, et al., Journal of the American Chemical Society, 104, 3607-3617 (1982).

General Procedure for Synthesis of 3-substituted tetrahydro-β-carbolines

NPM inhibitor Compounds 1 and 3-5 contain N-alkylated 3-substituted tetrahydro-β-carbolines and their synthetic routes differ from that of NSC348884. These compounds may be synthesized by a process such as that exemplified below for synthesis of Compound 4.

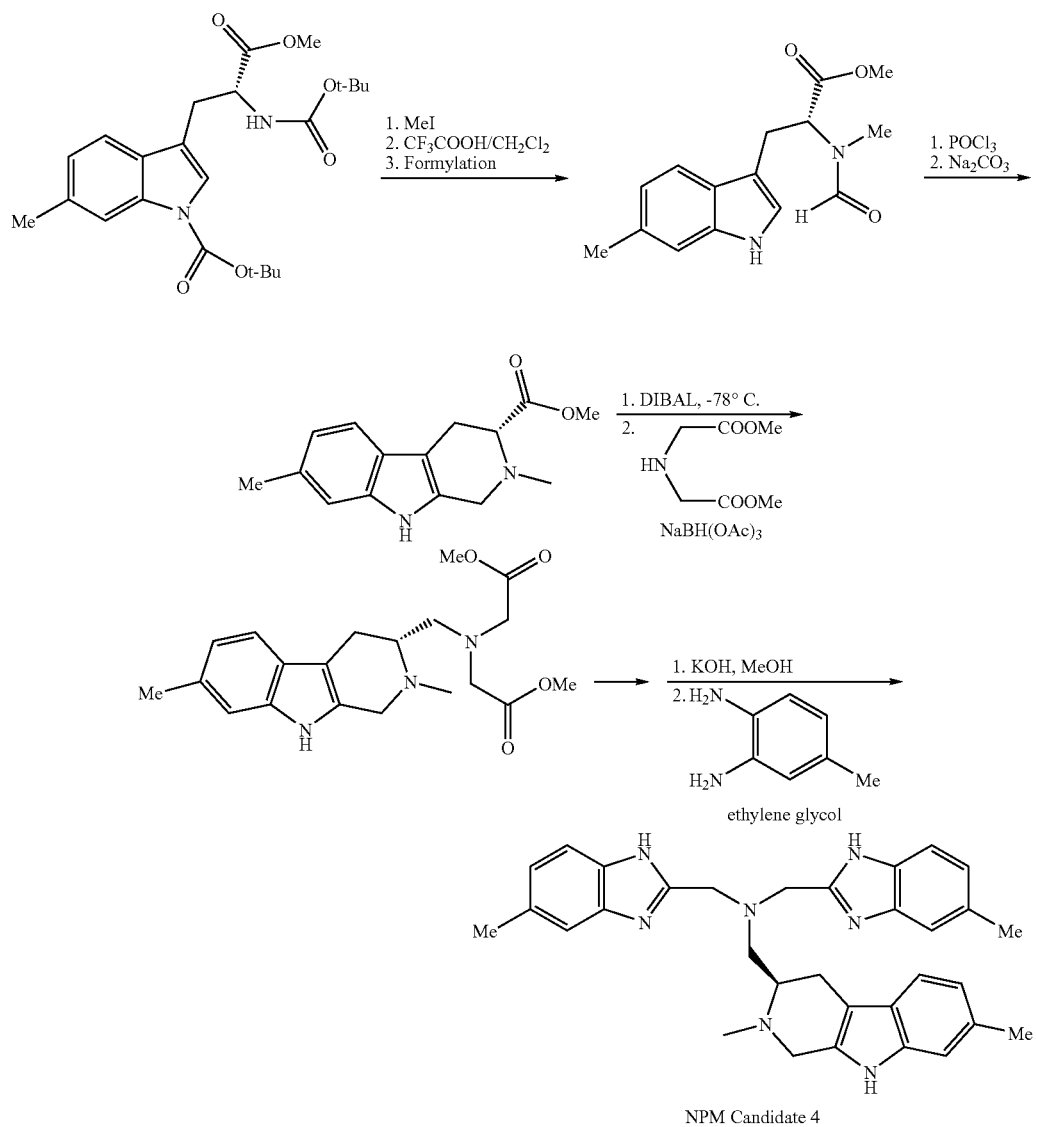

NPM Candidate 4

The initial step in the synthesis involves methylation of Boc-protected D-tryptophan methyl ester, followed by removal of the Boc protecting group and N-formylation. Next, Bieschler-Napieralski cyclization is carried out at room temperature using POCl$_3$ without co-solvent by following the method of Hino. The resulting methyl ester of 2-methyltetrahydro-β-carboline-3-carboxylic acid is reduced to aldehyde with DIBAL at low temperature and subjected to reductive amination. Next, the intermediate is condensed with two equivalents of 4-methyl 1,2-phenylenediamine in ethylene glycol at reflux to yield NPM candidate 4. Methods are procedures useful for producing the compounds of the invention are also incorporated by reference to Ohba, et al., *Tetrahedron Letters* 45, 6471-6474 (2004) and Ohba, et al., *Tetrahedron* 63, 10337-10344 (2007).

Screening Method Based on the Identification of the Multimerization Site/Hydrophobic Pocket in the N-Terminal Residues of Nucleophosmin Other small molecule inhibitors of NPM activity may be initially identified by in silico screening of small molecule databases. The human NPM dimer interface comprising of the interactions shown the table below was used to generate a 'Pharmacophore' for in Silico screening of large small molecular databases.

Homology Modeling, Pharmacophore Design, In Silico Screening and Drug Discovery. NPM forms dimers and higher oligomers via its N-terminal globular domain (amino acid residues 1-110). Since there is no crystal structure available for human NPM a homology model of the human NPM was built utilizing "Modeller" on a Linux workstation (http://salilab.org/modeller) utilizing the highly homologous Xenopus NO38-core chaperone structure (pdb:1XE0) (Namboodiri et al., 2004). The model was energy minimized (Sybyl V7.3, Tripos, Mo.) and analyzed by Procheck V3.5 (on the world wide web at: biochem.ucl.ac.uk/~roman/procheck) and Ramachandran plot for correctness and outliers.

Inspection of the human NPM homology model showed that the dimer interface revealed a highly conserved well defined hydrophobic-aromatic pocket. The inventors utilized the aromatic hydrophobic interactions between the NPM dimer to design a 'pharmacophore' to disrupt the dimer and hence NPM function.

| Interactions | Distance (in Angstroms) |
|---|---|
| Tyr 6 (Chain A)-Tyr 161 (Chain B) | 4.746 |
| His 29 (Chain A)-His 104 (chain A) | 3.76 |
| His 104 (Chain A)-Tyr 161 (Chain B) | 3.239 |
| His 104 (Chain A)-Phe 20 (Chain A) | 3.563 |
| Leu 7 (Chain A)-Met 159 (Chain B) | 2.985 |

Several large small molecular databases (NCI, Maybridge, LeadQuest and the Available Chemical Database) were screened using a 'Unity' search in Sybyl V7.3 (Tripos, Mo.). The top hits were interactively docked utilizing FlexX (Sybyl V7.3), ranked and interactions analyzed with respect to affinity of binding (T-score, C-score) and energy of binding (X-score).

In silico screening of large small molecular databases (>3 million compounds) targeting the highly conserved aromatic-hydrophobic interactions of the NPM dimer interface—residue interactions—provides a robust method for identifying novel small molecule inhibitors. Such small molecule inhibitors may be tested further in vitro or in vivo for their ability to inhibit oligomerization of NPM or for their anticancer properties.

EXAMPLES

Example 1

Structure-Based Discovery of Small Molecular Inhibitors of NPM

NPM forms dimers and higher oligomers via its N-terminal globular domain (residues 1-110) (FIG. 1A, Hingorani et al., 2000). The inventors sought out a small molecular inhibitor (SMI), targeting protein-protein interactions of the dimer interface that would inhibit NPM function. Since there is no crystal structure available for human NPM, a homology model of human NPM was built according to the Xenopus NO38-core chaperone structure (residues 1-107) (pdb:1XE0) (Namboodiri et al., 2004), which has a sequence identity of 77% and similarity of >90%. The homology model of NPM demonstrated a highly conserved topology and side-chain interactions of the dimer interface in comparison to Xenopus NO38-core structure. Inspection of the subunit interface revealed a predominantly hydrophobic-aromatic interaction that promotes the formation of a dimer and pentamer. Residues Tyr6, Lue7, Phe20, His29, Met53, Tyr55 and His104 are intimately involved in dimer formation and are essentially conserved except for Tyr6 (Phe) and Met 53 (Ile) in Xenopus (NO38) which are conservative changes (FIG. 1B). The 2 histidines and 3 aromatic residues form a hydrophobic interaction network was exploited for disruption by a specific SMI. A 'pharmacophore' based in silico screen of a large small molecular library ('Unity' search in Sybyl 7.3) identified several putative small molecules of which NSC348884 (di-[(((6-methyl-1H-benzo[d]imidazol-2-yl)methyl)((5-methyl-3-oxo-3H-indol-2-yl)methyl)]aminoethane, Mol. mass: 637.0 g/mol) was the top hit that docked with excellent hydrogen bonding and hydrophobic interactions (FIG. 1C, D).

Example 2

NSC348884 Disrupts NPM Oligomer Formation

Figure 2E:
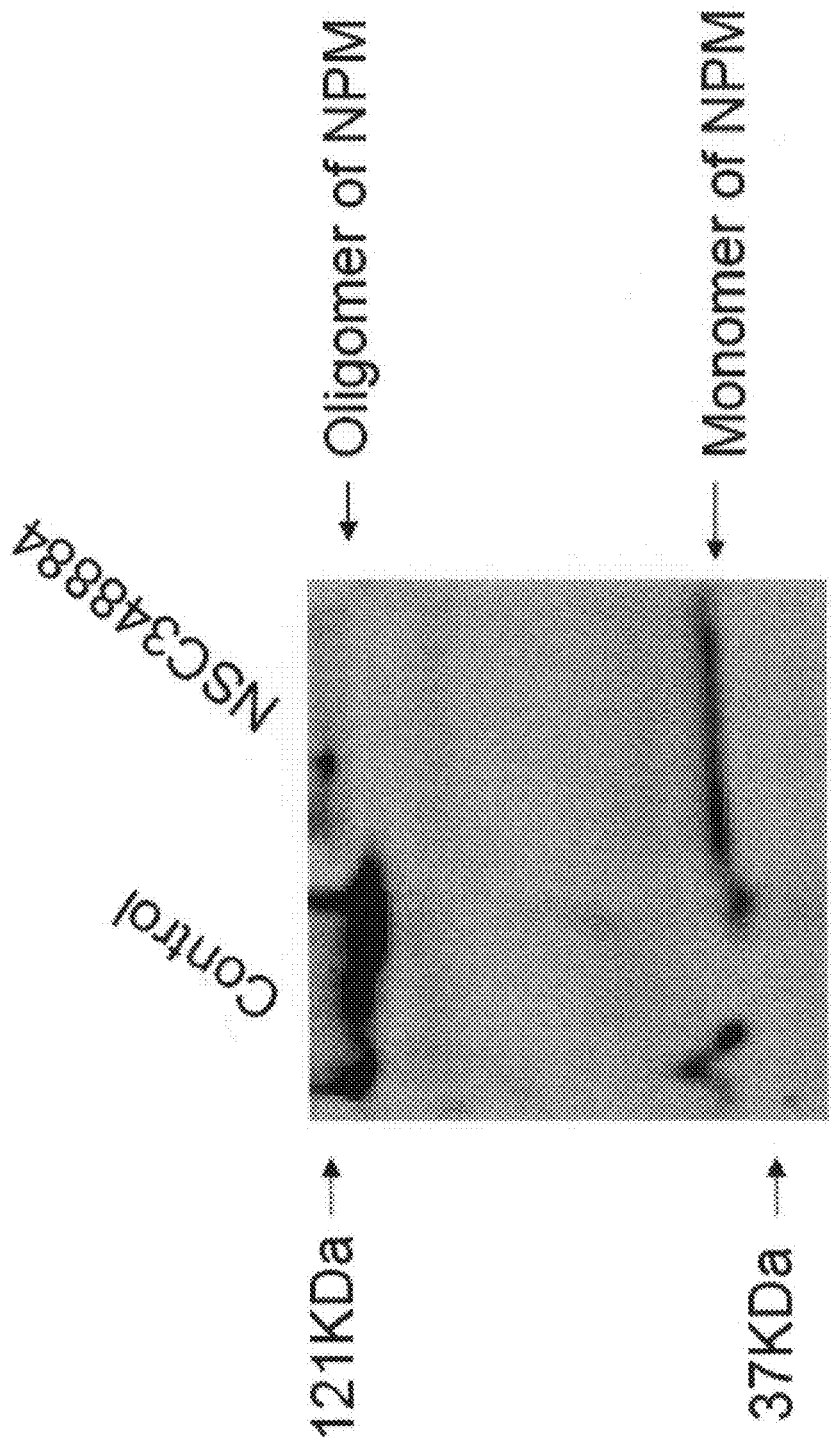

To examine whether NSC348884 specifically interacts with NPM and disrupts its oligomer formation, LNCaP and HCT116 cells with wild type NPM (no translocations) were treated with varying concentrations of NSC348884 (0, 5, 6 µM) for 24 hr, lyzed under non-denaturing conditions and analyzed by native PAGE which is an excellent tool for detecting oligomers and aggregates since the protein retains its folded conformation. We utilized 14-3-3 which forms dimers as a control. FIG. 2 shows that in both LNCaP and HCT116 cells, the NPM oligomer is disrupted with the formation of NPM monomers (FIG. 2A, FIG. 2C and FIG. 2E) at 5 and 6 ⌈M NSC348884, with no effect on the 14-3-3 dimer formation (Mr ~60 kDa) (FIG. 2B) in these cells. The two bands shown in HCT116 represent different isoforms of 14-3-3 proteins. Taken together, NSC348884 is able to bind to NPM and interfere with oligomer formation of NPM specifically.

Example 3

Inhibition of NPM is Cytotoxic and Synergizes with Doxorubicin

Figure 1D:
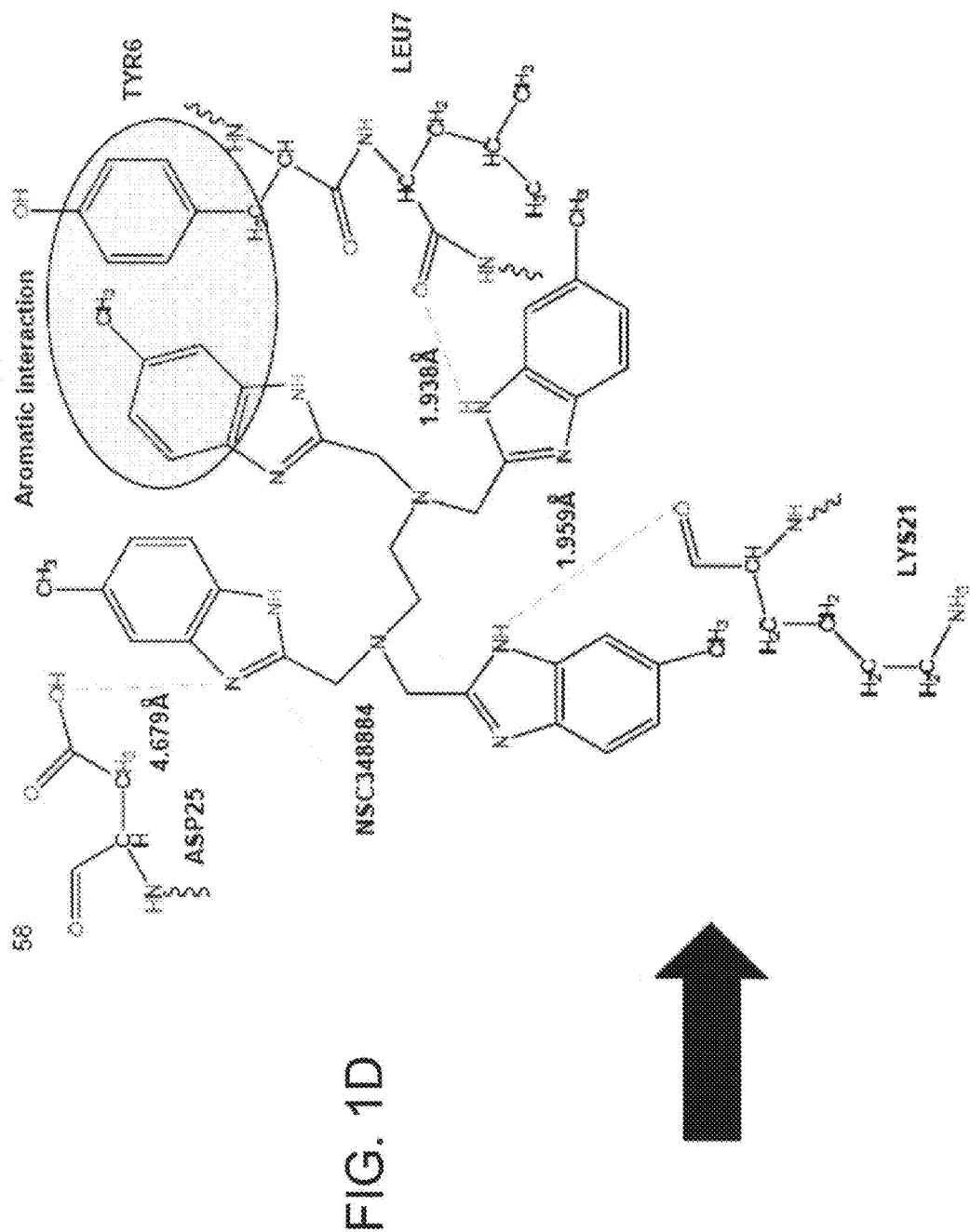
Figure 3A:
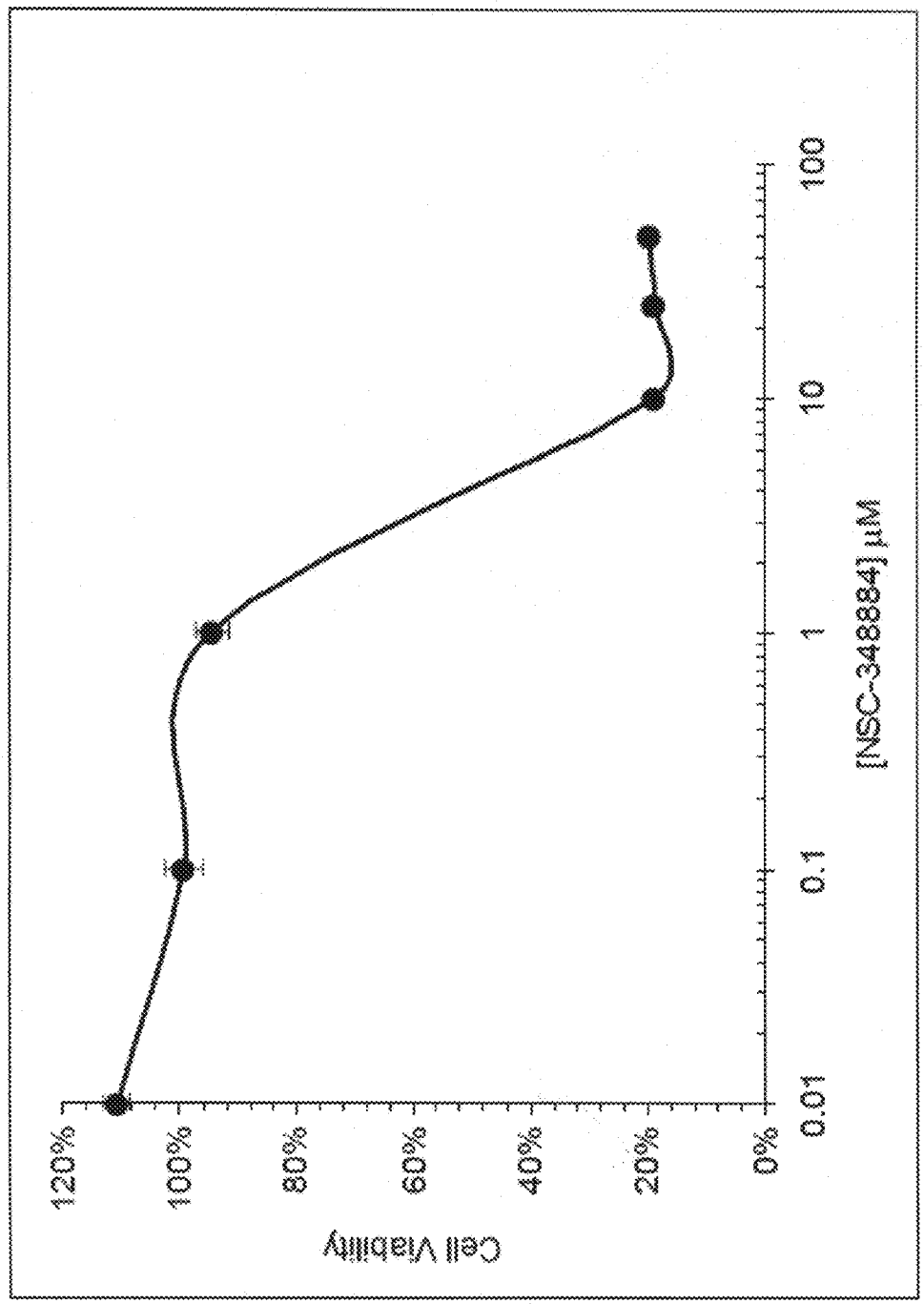
FIGS. 3A, 3B, 3C and 3D. Efficacy of NSC348884 in Cell Viability.
Figure 3B:
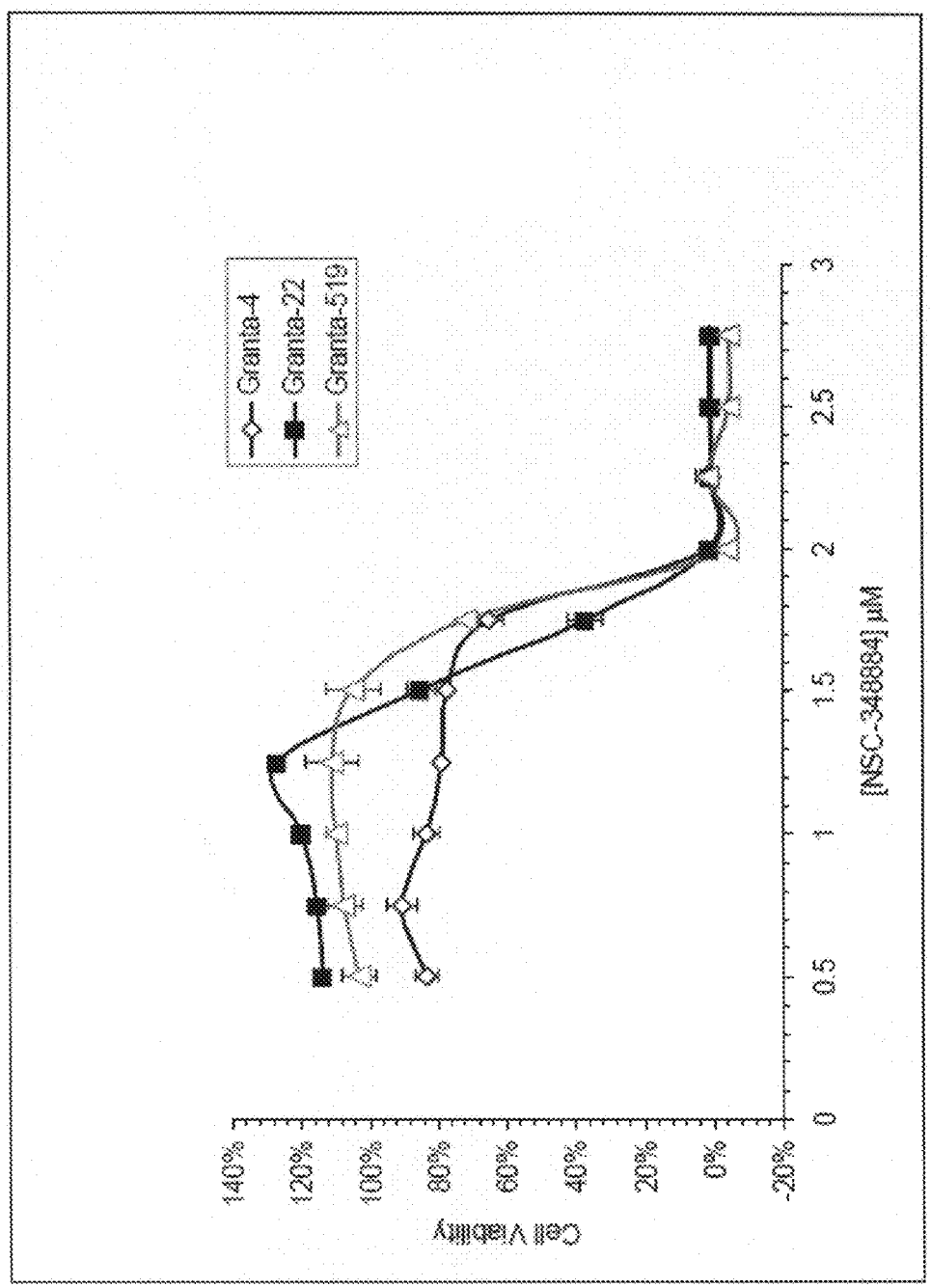
Figure 3C:
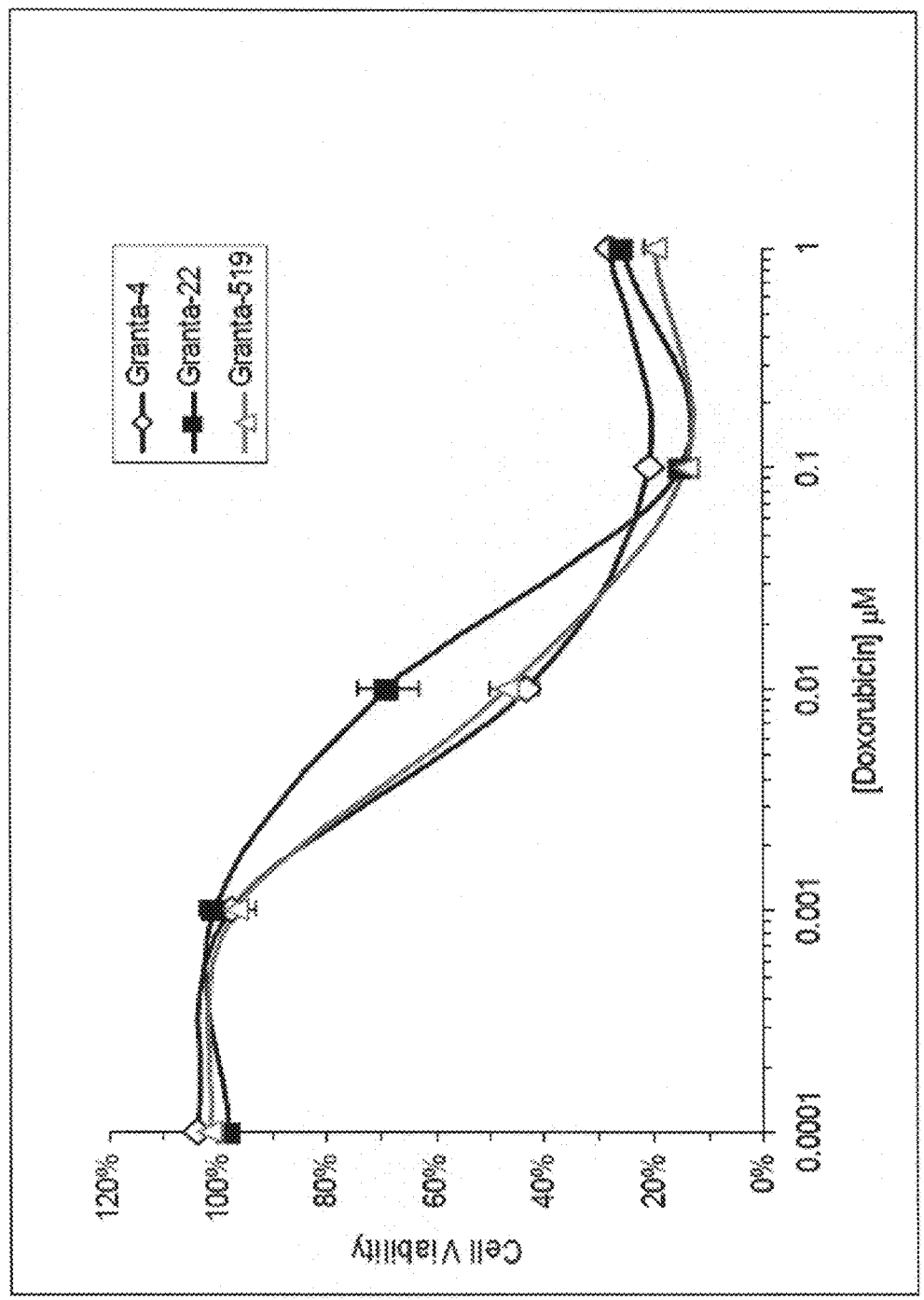
Figure 3D:
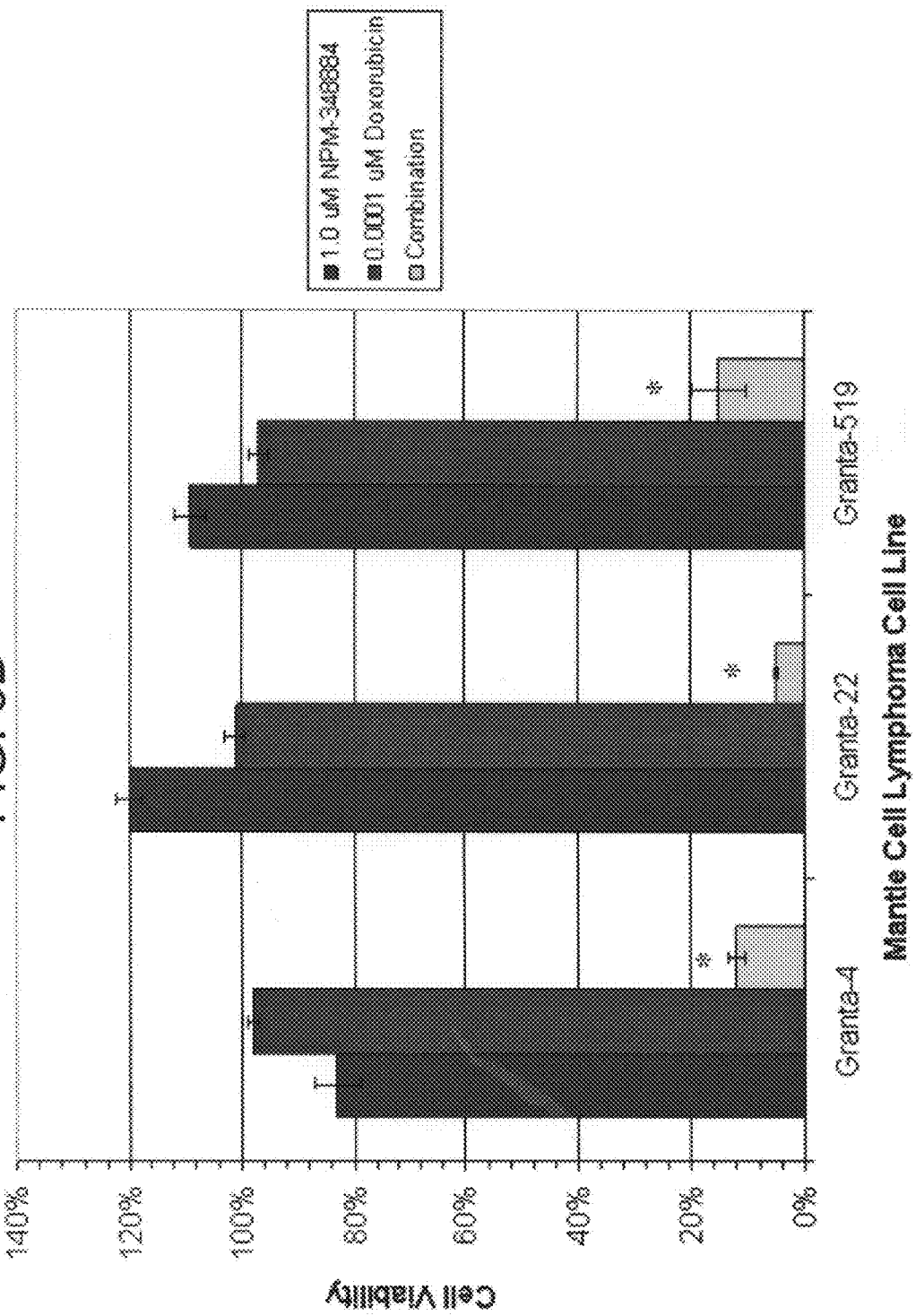

NPM plays an essential role in cellular activities such as ribosome biogenesis, cell proliferation, apoptosis and centrosome duplication. Therefore, inhibition of NPM should affect cell growth. To determine the effect of NPM inhibitor NSC348884 on cancer cell proliferation, cell viability assays were conducted on LNCaP and Granta (human mantle cell lymphoma) cells (Granta-519, -4, -22) with varying concentrations of NSC348884 over 4 days. In LNCaP cells the $IC_{50}$ for cell viability was ~4 µM (FIG. 3A), while for the 3 Granta cell lines the $IC_{50}$ was ~1.7 µM (FIG. 3A). The difference in $IC_{50}$ is attributed to the differential proliferative capacity of the two types of cancer cell lines. Since Rev peptide binds to NPM and potentates the doxorubicin-induced decrease of cellular viability and inhibition of tumor growth in nude mice (Chan et al., 2005), we evaluated if NSC348884 would be additive or synergistic with doxorubicin, a therapy commonly used in this disease. An $IC_{50}$ of 0.01-0.02 µM for doxorubicin was established for all 3 Granta cell lines, while at 0.1 nM doxorubicin had no effect on cell viability (FIG. 3A). As seen in FIG. 3A, 1 µM NSC348884 had no effect on cell viability at 4 days in a MTT assay. However, when all three Granta cell lines are exposed to 1 µM NSC348884 and 0.1 nM doxorubicin there was exquisite synergy with nearly complete loss of cell viability (FIG. 3B).

Cells and Reagents. Human cancer cell lines used herein include prostate (LNCaP, PC3, DU145), colon (HCT116), lung (A549), breast (MCF7) purchased from American Type Culture Collection (Rockville, Md.) and mantle cell lymphoma (Granta-4, -22 and -519) were maintained in RPMI 1640 medium (Mediatech, Va.) supplemented with 10% fetal bovine serum, 2 mM sodium pyruvate and 100 units/ml penicillin/streptomycin at 37° C. in a humidified atmosphere of 5% $CO_2$. Anti-nucleophosmin/B23 (C-19), anti-PARP (H-250), anti-p21 (F-5) and anti-14-3-3 (H-8) antibodies were obtained from Santa Cruz (Santa Cruz, Calif.). Anti-p53 (DO-1) antibody was from Calbiochem (San Diego, Calif.). Anti-phospho-p53 (Ser15) was from Cell Signaling (Danvers, Mass.). Anti-phospho-H2AX(Ser139) was purchased from Upstate (Lake pacific, NY). Anti-β-actin antibody and DAPI were from Sigma (St Louis, Mo.).

Cell Viability Assays. LNCaP, Granta-4, Granta-22 and Granta-519 cell lines were seeded into 96-well tissue culture plates with 50,000 cells per well, cultured for 24 hours and exposed to NSC348884, doxorubicin or combination for four days. All studies were performed in triplicate and were repeated 3 different times. After incubation, 20 µL of 2 mg/mL 3-(4,5-dimethylthiazol-2-yl)-2,5-diphenyltetrazolium bromide (MTT) were added to each well and incubated an additional four hours. The media and MTT dye were aspirated, and 100 µL dimethyl sulfoxide (DMSO) was added to each well, absorbance was read at 540 nm on a plate reader (Wallac Vector, PerkinElmer). Data was expressed as the percent survival of control calculated from the absorbance, corrected for background.

Immunoblotting. LNCaP or HCT116 cells were lysed in NP-40 lysis buffer containing 50 mM Tris-Cl (pH 7.4), 0.15 M NaCl, 0.5% NP-40, 1 mM DTT, 50 mM sodium fluoride and 2 µl/ml of a protease inhibitor cocktail (Sigma, St. Louis, Mo.). Protein concentrations were-determined using the Bio-Rad protein assay kit (Hercules, Calif.) and 50 µg of protein was resolved by electrophoresis on a 10% SDS-PAGE. The proteins were then transferred onto a nitrocellulose membrane and nonspecific binds were blocked by incubating with 5% nonfat milk in TBST buffer (0.01 M Tris-Cl, pH 8.0, 0.15 M NaCl, 0.5% Tween-20) at room temperature for 1 hr. The membrane was subjected to the indicated antibodies and the proteins were detected by the SuperSignal West Pico detection system (Pierce, Rockford, Ill.). For native PAGE gel experiment, the samples were not denatured by heating and the electrophoresis was run in the absence of SDS.

Statistical Analysis. Statistical comparisons were performed by Student's two-tailed t test. $P<0.05$ was considered to be significant.

Example 4

NSC348884 Induces Apoptosis

It has been reported that NPM prevents apoptosis (Grisendi et al., 2006; Ye, 2005). To examine whether disruption of NPM by NSC348884 correlates to apoptotic cell death, several cancer cell lines were treated with NSC348884 and apoptosis was determined by different methods.

Figure 4A:
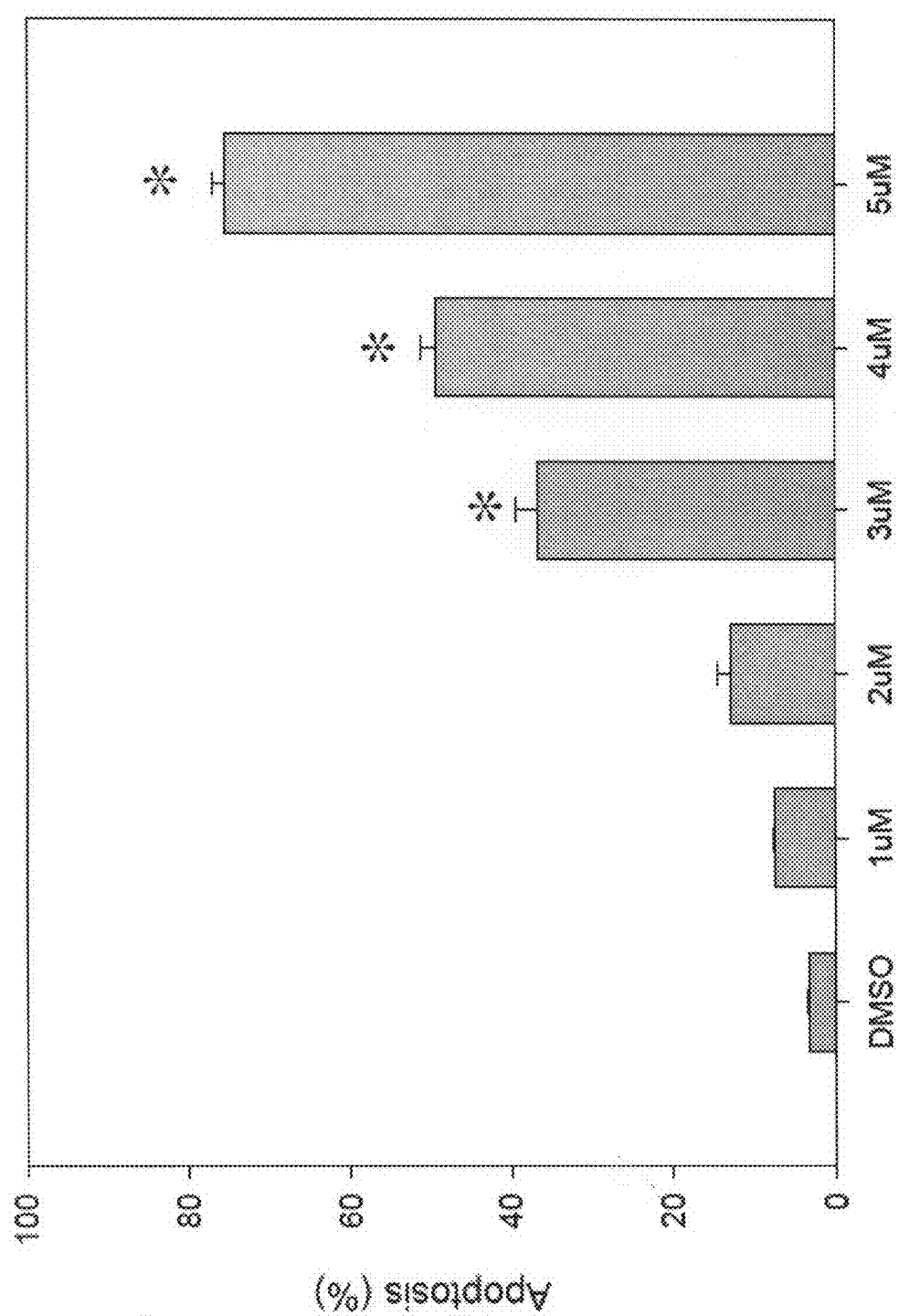
FIGS. 4A, 4B, 4C and 4D. NSC348884 induces apoptosis in several cancer cell lines.
Figure 4B:
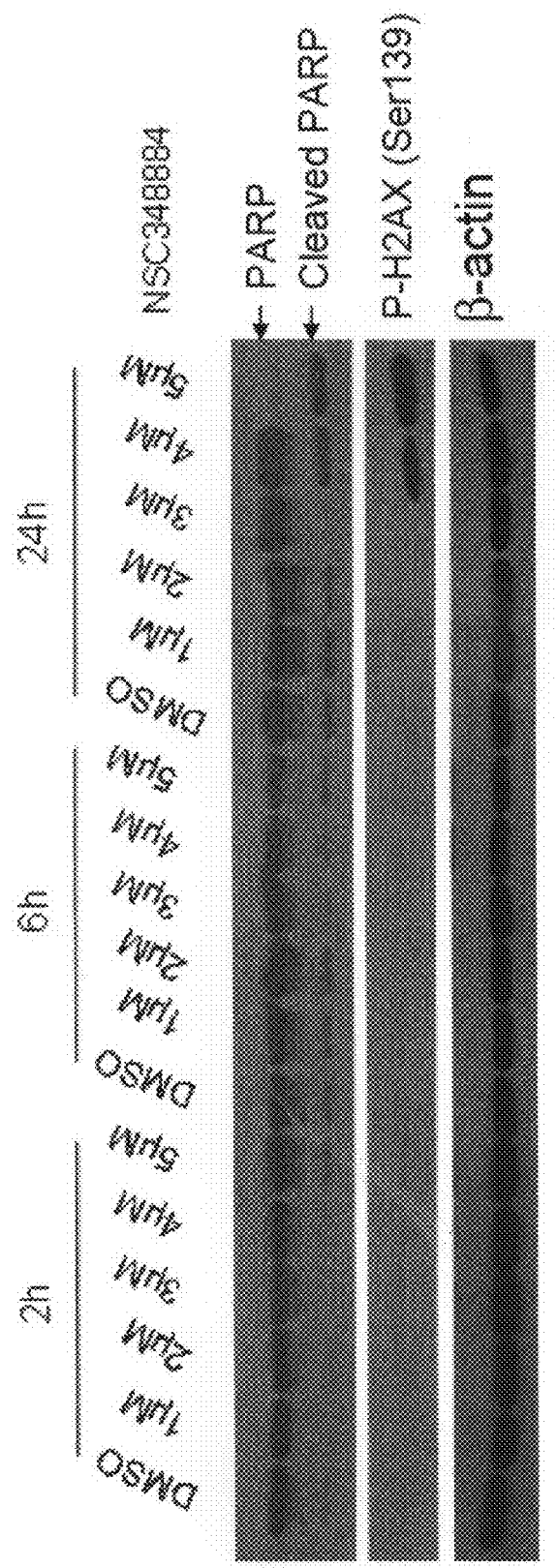

Treatment of LNCaP cells with varying concentrations of NSC348884 (0, 1, 2, 3, 4, 5 µM) showed a dose-dependent increase in apoptosis by morphology assay (FIG. 4A). Apoptosis by morphology was marked (>50%) at an exposure of 4 and 5 µM NSC348884 which correlated well with PARP-cleavage and induction H2AX phosphorylation (Liu et al., 2007) on Ser139 (FIG. 4B). Hence, together the data support the notion that apoptosis is completed at 24 hr at a dose of 4 to 5 µM NSC348884, which appears the mirror the $IC_{50}$ for cell viability (FIG. 3A).

Figure 4C:
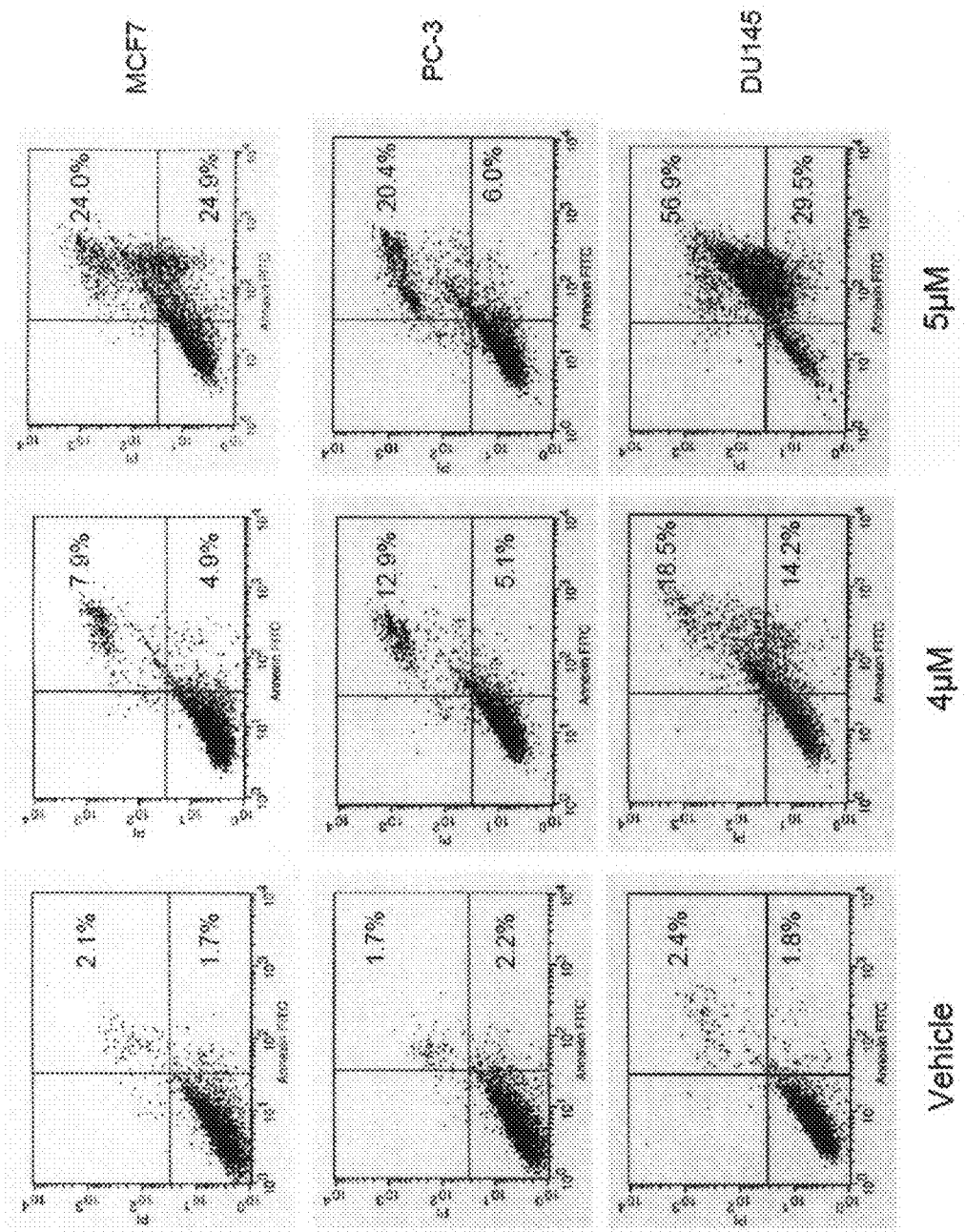
Figure 4D:
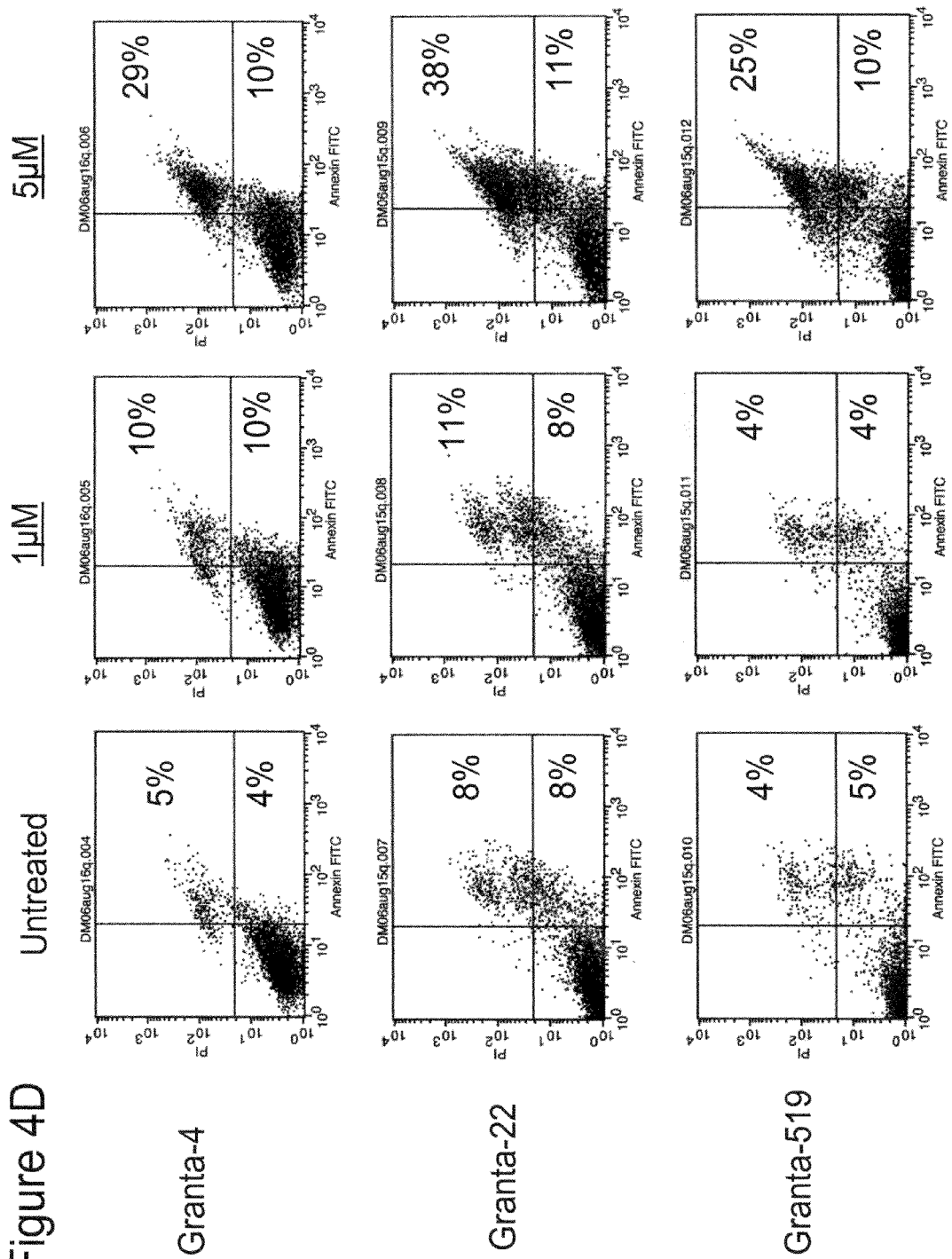

Furthermore, apoptosis induced by NSC348884 was confirmed by Annexin V staining and flow cytometry (FACS) analysis. As shown in FIG. 4C, NSC348884 induced apoptosis in several different cancer cell lines as evident by an increase in Annexin V binding which indicates phosphatidylserine translocation to the outer membrane. Collectively, these data demonstrate that NPM inhibitor, NSC348884 inhibits cell proliferation and elects apoptosis in a variety of cancer cell lines.

Apoptosis Assays. Drug treated LNCaP cells were examined for apoptotic morphology using a fluorescence staining technique as described previously (Qi and Martinez, 2003). Briefly, cells were exposed to DMSO or 1 to 5 µM of NSC348884 for 24 hr and were harvested by trypsinization. After staining with a mixed dye solution containing 100 mg/ml each of acridine orange and ethidium bromide the morphology of the cells were observed by fluorescence microscopy, and the number of apoptotic cells was quantified. Studies were performed in triplicate and mean+SD calculated. In all cases a minimum of 200 cells were counted for each sample. Using Annexin V staining to detect apoptosis, treated MCF-7, PC-3, DU145 and Granta (−519, −4, −22) cells were harvested by trypsinization and rinsed with cold PBS once. After centrifugation for 5 min, cancer cells were resuspended in 500 µl of 1 Annexin V binding buffer (BioVision, Annexin V-FITC Reagent Kit, Cat. #1001-1000) and then added 1 µl of Annexin V-FITC and 1 µl of Propidium Iodide (BioVision, Annexin VFITC Reagent Kit). After incubation for 5 min at room temperature in the dark, the samples were analyzed by flow cytometry.

Example 5

NSC348884 Upregulates p53

Figure 5A:
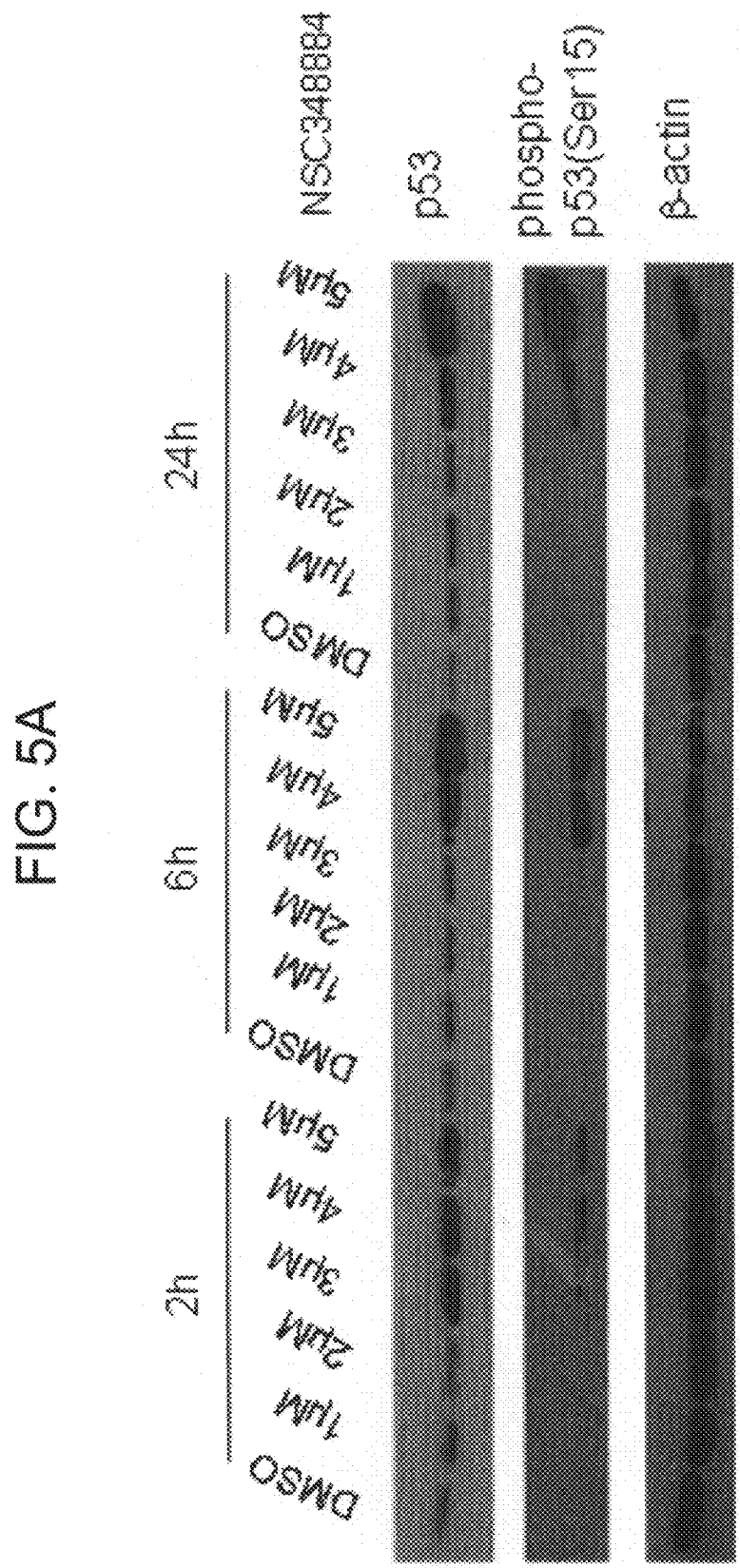

Mounting evidences indicate that NPM negatively regulates tumor suppressor p53 through interaction with p53 directly to prevent its phosphorylation on Ser15 (Maiguel et al., 2004) or through binding with $p14_{ARF}$ to impair the ARF-Hdm2 association and increase Hdm2/p53 complex formation (Gjerset, 2006). NPM knockdown by small interfering RNA enhances p53 phosphorylation and transcriptional activity. Therefore, inhibition of NPM by NSC348884 could affect p53 status. To address this, LNCaP cells were untreated and treated with different dosage of NSC348884 for 2 h to 24 h, and the changes in p53 protein and phosphorylation levels were determined by Western blot. Indeed, NSC348884 increased both p53 protein level and phosphorylation on Ser15 in a dose-dependent manner after 2 h of incubation (FIG. 5A). Moreover, p21, a key transcriptional target of p53 was also up-regulated by NSC348884 (FIG. 5B), suggesting inhibition of NPM elevated p53 transcriptional activity. Similarly, NSC348884 also enhanced p53 in breast cancer cell line MCF7. Consistent with this, immunocytochemistry staining showed that higher p53 proteins were induced by NSC348884 treatment compared to vehicle incubation in LNCaP and A549 cancer cells (FIG. 5C). Moreover, the p53 signals were located in nucleus, suggesting p53 has functions after NSC348884 incubation.

Immunocytochemistry. LNCaP, A549 or HCT116 cells grown on cover slips were treated with DMSO or 5 µM of NSC348884 for 6 hr and then fixed in cold methanol:acetone (3:7) for 5 minutes. The cover slips were washed twice with cold PBS and blocked with blocking buffer (1% BSA, 0.01% saponin and 1% normal mouse serum in PBS) for 1 hr at room temperature. The cover slips were then immunostained using anti-p53 antibody at the dilution 1:100 in blocking buffer overnight at 4° C. After washing 3 times with PBS, the secondary antibody conjugated with Cy3 (Sigma) was applied for 30 min at room temperature. The cover slips were washed three times by PBS and counterstained by DAPI (0.1 µg/ml) for 1 min. Finally, the signal was checked using florescence microscopy. Primary or secondary antibody replacement with normal serum from the same animal species was used as the negative controls.

Example 6

Figure 6:
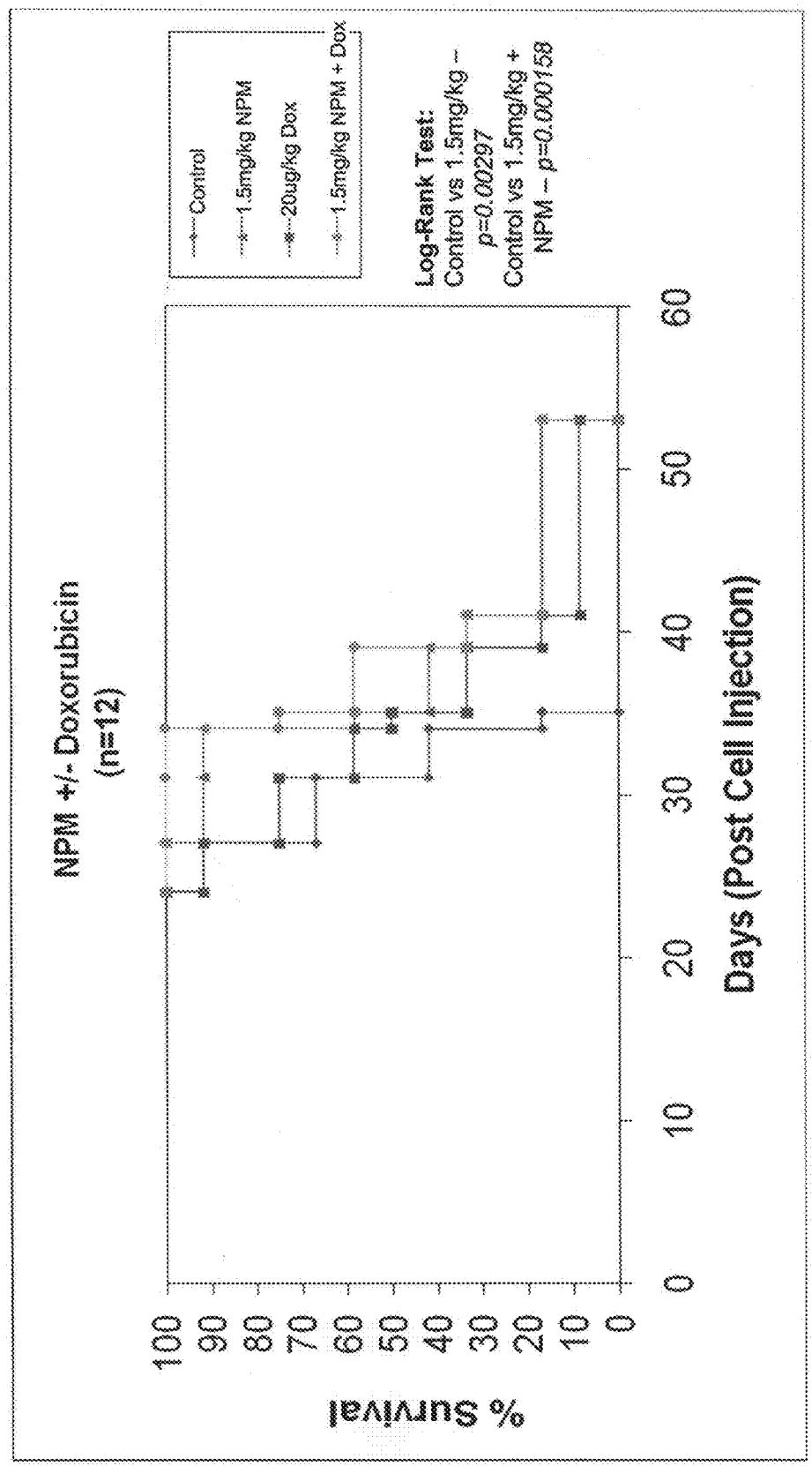
FIG. 6. Comparative survival of mice inoculated with HCT116 colon cancer cells and treated with NSC348884 or NSC348884/doxorubicin compared to control.

In Vivo Model in SCID Mouse of Use of Small Molecule Inhibitor of NPM NSC348884 to Treat Human Colon Cancer (HCT116) with and without Doxorubicin SCID mice were inoculated with $10\times10^6$ HCT116 colon cancer cells in their flanks to form measurable tumors in the range 60-100 $mm^3$. Mice were pair matched with 12 mice per arm. NSC348884 was administered (Monday, Wednesday, Friday), Doxorubicin (Monday), combination or vehicle by intra-peritoneal injection each for 4 weeks. Measurements of tumor growth were performed twice a week and tumor volume estimated according to the formula: [(width)$^2$×length]/2. Mice were weighed before the beginning of the experiment and twice a week thereafter to check for signs of toxicity. Control mice (upper panel, first bar) were treated with vehicle (DMSO), NSC348884 at 1.5 mg/kg NSC348884 (upper panel, second bar), very low dose doxorubicin at 20 ug/kg (upper panel, third bar), and the combination of NSC348884/doxorubicin (upper panel, fourth bar). All animals in the control group (lower panel) reached approximately 2000 mm$^3$ at day 30 and were sacrificed per protocol recommendation. All mice except for 1 treated with doxorubicin (lower panel) were all dead at day 41. However, mice treated with NSC348884 or NSC34884/doxorubicin combination lived to 53 days (FIG. 6). These data clearly show a statistically significant survival advantage with NSC348884 alone and NSC348884/doxorubicin combination. These data are reflected in the mean tumor growth inhibition (TGI) data shown in FIG. 7. The mean TGI was ~40-50% with NSC348884 alone or with the combination. Moreover, there were no discernible toxicities observed between the control and treated animals including weight loss >10%. These data clearly show that NSC348884 is an active anti-cancer drug molecule and can be combined with chemotherapy safely.

REFERENCES

Ahn J Y, Liu X, Cheng D, Peng J, Chan P K, Wade P A et al (2005). Nucleophosmin/B23, a nuclear PI(3,4,5)P(3) receptor, mediates the antiapoptotic actions of NGF by inhibiting CAD. *Mol Cell* 18: 435-45.

Arkin M R, Wells J A (2004). Small-molecule inhibitors of protein-protein interactions: progressing towards the dream. *Nat Rev Drug Discov* 3: 301-17.

Bertwistle D, Sugimoto M, Sherr C J (2004). Physical and functional interactions of the Arf tumor suppressor protein with nucleophosmin/B23. *Mol Cell Biol* 24: 985-96.

Brady S N, Yu Y, Maggi L B, Jr., Weber J D (2004). ARF impedes NPM/B23 shuttling in an Mdm2-sensitive tumor suppressor pathway. *Mol Cell Biol* 24: 9327-38.

Chan H J, Weng J J, Yung B Y (2005). Nucleophosmin/B23-binding peptide inhibits tumor growth and up-regulates transcriptional activity of p53. *Biochem Biophys Res Commun* 333: 396-403.

Chan W Y, Liu Q R, Borjigin J, Busch H, Rennert O M, Tease L A et al (1989). Characterization of the cDNA encoding human nucleophosmin and studies of its role in normal and abnormal growth. *Biochemistry* 28: 1033-9.

Chou Y H, Yung B Y (1995). Cell cycle phase-dependent changes of localization and oligomerization states of nucleophosmin/B23. *Biochem Biophys Res Commun* 217: 313-25.

Colombo E, Bonetti P, Lazzerini Denchi E, Martinelli P, Zamponi R, Marine J C et al (2005). Nucleophosmin is required for DNA integrity and p19Arf protein stability. *Mol Cell Biol* 25: 8874-86.

Colombo E, Marine J C, Danovi D, Falini B, Pelicci P G (2002). Nucleophosmin regulates the stability and transcriptional activity of p53. *Nat Cell Biol* 4: 529-33.

Fankhauser C, Izaurralde E, Adachi Y, Wingfield P, Laemmli U K (1991). Specific complex of human immunodeficiency virus type I rev and nucleolar B23 proteins: dissociation by the Rev response element. *Mol Cell Biol* 11: 2567-75.

Feuerstein N, Chan P K, Mond J J (1988). Identification of numatrin, the nuclear matrix protein associated with induction of mitogenesis, as the nucleolar protein B23. Implication for the role of the nucleolus in early transduction of mitogenic signals. *J Biol Chem* 263: 10608-12.

Gjerset R A (2006). DNA damage, p14ARF, nucleophosmin (NPM/B23), and cancer. *J Mol Histol* 37: 239-51.

Grisendi S, Mecucci C, Falini B, Pandolfi P P (2006). Nucleophosmin and cancer. *Nat Rev Cancer* 6: 493-505.

Herrera J E, Correia J J, Jones A E, Olson M O (1996). Sedimentation analyses of the salt and divalent metal ion-induced oligomerization of nucleolar protein B23. *Biochemistry* 35: 2668-73.

Hingorani K, Szebeni A, Olson M O (2000). Mapping the functional domains of nucleolar protein B23. *J Biol Chem* 275: 24451-57.

Itahana K, Bhat K P, Jin A, Itahana Y, Hawke D, Kobayashi R et al (2003). Tumor suppressor ARF degrades B23, a nucleolar protein involved in ribosome biogenesis and cell proliferation. *Mol Cell* 12: 1151-64.

Kondo T, Minamino N, Nagamura-Inoue T, Matsumoto M, Taniguchi T, Tanaka N (1997). Identification and characterization of nucleophosmin/B23/numatrin which binds the anti-oncogenic transcription factor IRF-1 and manifests oncogenic activity. *Oncogene* 15: 1275-81.

Korgaonkar C, Hagen J, Tompkins V, Frazier A A, Allamargot C, Quelle F W et al (2005). Nucleophosmin (B23) targets ARF to nucleoli and inhibits its function. *Mol Cell Biol* 25: 1258-71.

Kurki S, Peltonen K, Latonen L, Kiviharju T M, Ojala P M, Meek D et al (2004). Nucleolar protein NPM interacts with HDM2 and protects tumor suppressor protein p53 from HDM2-mediated degradation. *Cancer Cell* 5: 465-75.

Lee C, Smith B A, Bandyopadhyay K, Gjerset R A (2005). DNA damage disrupts the p14ARF-B23(nucleophosmin) interaction and triggers a transient subnuclear redistribution of p14ARF. *Cancer Res* 65: 9834-42.

Li J, Zhang X, Sejas D P, Bagby G C, Pang Q (2004). Hypoxia-induced nucleophosmin protects cell death through inhibition of p53. *J Biol Chem* 279: 41275-9.

Li J, Zhang X, Sejas D P, Pang Q (2005). Negative regulation of p53 by nucleophosminantagonizes stress-induced apoptosis in human normal and malignant hematopoietic cells. *Leuk Res* 29: 1415-23.

Li Y P, Busch R K, Valdez B C, Busch H (1996). C23 interacts with B23, a putative nucleolar-localization-signal-binding protein. *Eur J Biochem* 237: 153-8.

Lim M J, Wang X W (2006). Nucleophosmin and human cancer. *Cancer Detect Prev* 30:481-90.

Liu Y, Tseng M, Perdreau S A, Rossi F, Antonescu C, Besmer P et al (2007). Histone H2AX is a mediator of gastrointestinal stromal tumor cell apoptosis following treatment with imatinib mesylate. *Cancer Res* 67: 2685-92.

Maiguel D A, Jones L, Chakravarty D, Yang C, Carrier F (2004). Nucleophosmin sets a threshold for p53 response to UV radiation. *Mol Cell Biol* 24: 3703-11.

Namboodiri V M, Akey I V, Schmidt-Zachmann M S, Head J F, Akey C W (2004). The structure and function of Xenopus NO38-core, a histone chaperone in the nucleolus. *Structure* 12: 2149-60.

Naoe T, Suzuki T, Kiyoi H, Urano T (2006). Nucleophosmin: a versatile molecule associated with hematological malignancies. *Cancer Sci* 97: 963-9.

Nozawa Y, Van Belzen N, Van der Made A C, Dinjens W N, Bosman F T (1996). Expression of nucleophosmin/B23 in normal and neoplastic colorectal mucosa. *J Pathol* 178: 48-52.

Okuda M (2002). The role of nucleophosmin in centrosome duplication. *Oncogene* 21:6170-4.
Okuwaki M, Matsumoto K, Tsujimoto M, Nagata K (2001). Function of nucleophosmin/B23, a nucleolar acidic protein, as a histone chaperone. *FEBS Lett* 506:272-6.
Oltersdorf T, Elmore S W, Shoemaker A R, Armstrong R C, Augeri D J, Belli B A et al (2005). An inhibitor of Bcl-2 family proteins induces regression of solid tumours. *Nature* 435: 677-81.
Oost T K, Sun C, Armstrong R C, Al-Assaad A S, Betz S F, Deckwerth T L et al (2004). Discovery of potent antagonists of the antiapoptotic protein XIAP for the treatment of cancer. *J Med Chem* 47: 4417-26.
Oren M (1999). Regulation of the p53 tumor suppressor protein. *J Biol Chem* 274: 36031-4.
Patterson S D, Grossman J S, D'Andrea P, Latter G I (1995). Reduced numatrin/B23/nucleophosmin labeling in apoptotic Jurkat T-lymphoblasts. *J Biol Chem* 270: 9429-36.
Qi W, Martinez J D (2003). Reduction of 14-3-3 proteins correlates with increased sensitivity to killing of human lung cancer cells by ionizing radiation. *Radiat Res* 160: 217-23.
Shields L B, Gercel-Taylor C, Yashar C M, Wan T C, Katsanis W A, Spinnato J A et al (1997). Induction of immune responses to ovarian tumor antigens by multiparity. *J Soc Gynecol Investig* 4: 298-304.
Subong E N, Shue M J, Epstein J I, Briggman J V, Chan P K, Partin A W (1999). Monoclonal antibody to prostate cancer nuclear matrix protein (PRO:4-216) recognizes nucleophosmin/B23. *Prostate* 39: 298-304.
Takemura M, Sato K, Nishio M, Akiyama T, Umekawa H, Yoshida S (1999). Nucleolar protein B23.1 binds to retinoblastoma protein and synergistically stimulates DNA polymerase alpha activity. *J Biochem (Tokyo)* 125: 904-9.
Tanaka M, Sasaki H, Kino 1, Sugimura T, Terada M (1992). Genes preferentially expressed in embryo stomach are predominantly expressed in gastric cancer. *Cancer Res* 52: 3372-7.
Valdez B C, Perlaky L, Henning D, Saijo Y, Chan P K, Busch H (1994). Identification of the nuclear and nucleolar localization signals of the protein p120. Interaction with translocation protein B23. *J Biol Chem* 269: 23776-83.
van Belzen N, Diesveld M P, van der Made A C, Nozawa Y, Dinjens W N, Vlietstra R et al (1995). Identification of mRNAs that show modulated expression during colon carcinoma cell differentiation. *Eur J Biochem* 234: 843-8.
Vassilev L T, Vu B T, Graves B, Carvajal D, Podlaski F, Filipovic Z et al (2004). In vivo activation of the p53 pathway by small-molecule antagonists of MDM2. *Science* 303:844-8.
Wang D, Umekawa H, Olson M O (1993). Expression and subcellular locations of two forms of nucleolar protein B23 in rat tissues and cells. *Cell Mol Biol Res* 39: 33-42.
Wang W, Budhu A, Forgues M, Wang X W (2005). Temporal and spatial control of nucleophosmin by the Ran-Crm1 complex in centrosome duplication. *Nat Cell Biol* 7: 823-30.
Ye K (2005). Nucleophosmin/B23, a multifunctional protein that can regulate apoptosis. *Cancer Biol Ther* 4: 918-23.
Yeh C W, Huang S S, Lee R P, Yung B Y (2006). Ras-dependent recruitment of c-Myc for transcriptional activation of nucleophosmin/B23 in highly malignant U1 bladder cancer cells. *Mol Pharmacol* 70: 1443-53.
Yung B Y, Bor A M, Chan P K (1990). Short exposure to actinomycin D induces "reversible" translocation of protein B23 as well as "reversible" inhibition of cell growth and RNA synthesis in HeLa cells. *Cancer Res* 50: 5987-91.
Zhang Y (2004). The ARF-B23 connection: implications for growth control and cancer treatment. *Cell Cycle* 3: 259-62.

The invention claimed is:

1. A method for treating cancer comprising administering an effective amount of a compound to a subject in need thereof, wherein said compound is NSC348884:

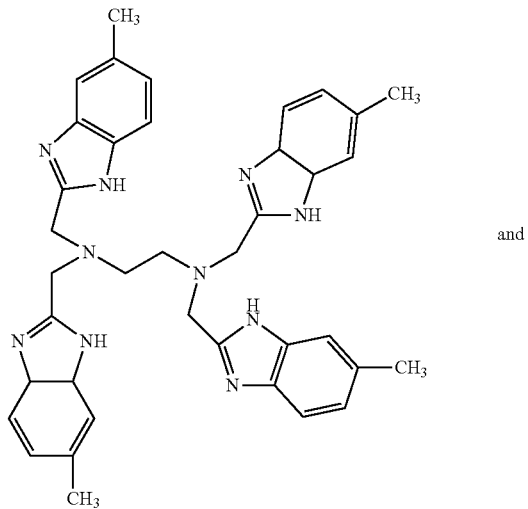

and wherein said subject in need thereof has a cancer selected from the group consisting of breast cancer, colon cancer, lung cancer, mantle cell lymphoma, and prostate cancer.

2. The method of claim 1, wherein said subject in need thereof has colon cancer.

3. The method of claim 1, wherein said subject in need thereof has lung cancer.

4. The method of claim 1, wherein said subject in need thereof has prostate cancer.

5. The method of claim 1, wherein said subject in need thereof has breast cancer.

6. The method of claim 1, wherein said subject in need thereof has mantle cell lymphoma.

7. The method of claim 1, further comprising administering to said subject a second type of anticancer therapy.

* * * * *